United States Patent
Franke et al.

(10) Patent No.: US 10,413,731 B2
(45) Date of Patent: Sep. 17, 2019

(54) SELECTIVE NERVE STIMULATION USING PRESYNAPTIC TERMINAL DEPLETION BLOCK

(71) Applicant: Cardiac Pacemakers, Inc., St. Paul, MN (US)

(72) Inventors: Manfred Franke, Weissenborn Sa. (DE); David J. Ternes, Roseville, MN (US); Juan Gabriel Hincapie Ordonez, Maple Grove, MN (US); Stephen B. Ruble, Lino Lakes, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/597,145

(22) Filed: Jan. 14, 2015

(65) Prior Publication Data
US 2015/0202446 A1    Jul. 23, 2015

Related U.S. Application Data

(60) Provisional application No. 61/928,732, filed on Jan. 17, 2014.

(51) Int. Cl.
 *A61N 1/00* (2006.01)
 *A61N 1/36* (2006.01)
 (Continued)

(52) U.S. Cl.
 CPC ........ *A61N 1/3611* (2013.01); *A61B 18/1206* (2013.01); *A61N 1/0551* (2013.01);
 (Continued)

(58) Field of Classification Search
 CPC ............ A61N 1/36128; A61N 1/36139; A61N 1/36067; A61N 1/36171; A61N 1/36053;
 (Continued)

(56) References Cited

U.S. PATENT DOCUMENTS

| 4,608,985 A | 9/1986 | Crish et al. |
|---|---|---|
| 5,421,817 A | 6/1995 | Liss et al. |

(Continued)

FOREIGN PATENT DOCUMENTS

| AU | 2015206540 B2 | 7/2007 |
|---|---|---|
| AU | 2015206541 B2 | 12/2017 |

(Continued)

OTHER PUBLICATIONS

Franke, Manfred, et al., "Depletion Block to Block Nerve Communication", U.S. Appl. No. 61/928,725, filed Jan. 17, 2014.
(Continued)

*Primary Examiner* — Mallika D Fairchild
(74) *Attorney, Agent, or Firm* — Schwegman Lundberg & Woessner, P.A.

(57) ABSTRACT

An example of a system may include a stimulator and at least one controller. The stimulator may be configured to deliver nerve stimulation to capture a first set of axons in a nerve and to deliver depletion block stimulation to capture a second set of axons in the nerve, where the second set is a subset of the first. The depletion block stimulation may include a series of pulses at a depletion pulse frequency within a range between about 100 Hz to about 1 kHz, and the nerve stimulation may include a series of pulses at a stimulation pulse frequency within a range of about 0.25 Hz to about 50 Hz. At least a portion of the nerve stimulation and at least a portion of the depletion block stimulation may be delivered to be effective in providing a nerve block while delivering nerve stimulation.

20 Claims, 21 Drawing Sheets

(51) Int. Cl.
| | | |
|---|---|---|
| *A61N 1/05* | (2006.01) | |
| *A61B 18/12* | (2006.01) | |
| A61B 18/00 | (2006.01) | |
| A61N 1/372 | (2006.01) | |
| A61N 1/378 | (2006.01) | |
| A61B 18/14 | (2006.01) | |
| A61B 18/20 | (2006.01) | |

(52) U.S. Cl.
CPC ....... *A61N 1/0558* (2013.01); *A61N 1/36053* (2013.01); *A61N 1/36067* (2013.01); *A61N 1/36071* (2013.01); *A61N 1/36117* (2013.01); *A61N 1/36128* (2013.01); *A61N 1/36171* (2013.01); *A61B 18/1477* (2013.01); *A61B 18/20* (2013.01); *A61B 2018/00577* (2013.01); *A61B 2018/00595* (2013.01); *A61N 1/36132* (2013.01); *A61N 1/36135* (2013.01); *A61N 1/3787* (2013.01); *A61N 1/37205* (2013.01); *A61N 1/37288* (2013.01)

(58) Field of Classification Search
CPC .......................... A61N 1/3611; A61N 1/0551; A61N 1/36071; A61N 1/0558; A61N 1/36117; A61N 1/36132; A61N 1/36288; A61N 1/3787; A61N 1/36135; A61N 1/37205; A61B 18/20; A61B 18/1206; A61B 18/1477; A61B 2018/00595; A61B 2018/00577
See application file for complete search history.

(56) References Cited

U.S. PATENT DOCUMENTS

| | | | |
|---|---|---|---|
| 7,389,145 B2 | 6/2008 | Kilgore et al. | |
| 7,734,355 B2 | 6/2010 | Cohen et al. | |
| 7,826,899 B1 | 11/2010 | Ryu et al. | |
| 7,949,399 B2 | 5/2011 | Wenzel et al. | |
| 8,060,208 B2 | 11/2011 | Kilgore et al. | |
| 8,229,564 B2 | 7/2012 | Rezai et al. | |
| 8,483,831 B1 | 7/2013 | Hlavka et al. | |
| 9,242,097 B2 | 1/2016 | Mokelke et al. | |
| 10,201,709 B2 | 2/2019 | Franke et al. | |
| 2002/0055779 A1 | 5/2002 | Andrews | |
| 2003/0233137 A1 | 12/2003 | Paul, Jr. | |
| 2004/0093093 A1 | 5/2004 | Andrews | |
| 2004/0111126 A1 | 6/2004 | Tanagho et al. | |
| 2004/0127953 A1 | 7/2004 | Kilgore et al. | |
| 2005/0021092 A1 | 1/2005 | Yun et al. | |
| 2005/0137644 A1* | 6/2005 | Boveja ............... | A61N 1/36053 607/40 |
| 2005/0149148 A1 | 7/2005 | King | |
| 2005/0216070 A1* | 9/2005 | Boveja ............... | A61N 1/08 607/46 |
| 2006/0200208 A1 | 9/2006 | Terry, Jr. et al. | |
| 2006/0253161 A1 | 11/2006 | Libbus et al. | |
| 2007/0027496 A1 | 2/2007 | Parnis et al. | |
| 2007/0073356 A1 | 3/2007 | Rooney et al. | |
| 2007/0191902 A1 | 8/2007 | Errico et al. | |
| 2007/0213771 A1 | 9/2007 | Spinner et al. | |
| 2008/0183248 A1 | 7/2008 | Rezai et al. | |
| 2008/0208305 A1 | 8/2008 | Rezai et al. | |
| 2009/0155336 A1 | 6/2009 | Rezai | |
| 2009/0204173 A1 | 8/2009 | Fang et al. | |
| 2009/0281593 A9 | 11/2009 | Errico et al. | |
| 2010/0023088 A1 | 1/2010 | Stack et al. | |
| 2010/0070004 A1 | 3/2010 | Hlavka et al. | |
| 2010/0094376 A1 | 4/2010 | Penner et al. | |
| 2010/0114261 A1 | 5/2010 | Errico et al. | |
| 2010/0191311 A1 | 7/2010 | Scheiner et al. | |
| 2010/0217347 A1 | 8/2010 | Swoyer et al. | |
| 2010/0228310 A1 | 9/2010 | Shuros et al. | |
| 2010/0241190 A1 | 9/2010 | Kilgore et al. | |
| 2010/0324630 A1 | 12/2010 | Lee et al. | |
| 2011/0009927 A1 | 1/2011 | Parker et al. | |
| 2011/0118725 A1 | 5/2011 | Mayse et al. | |
| 2011/0125216 A1 | 5/2011 | Kilgore et al. | |
| 2011/0184486 A1 | 7/2011 | De Ridder | |
| 2012/0059437 A1 | 3/2012 | Shalev | |
| 2012/0172680 A1 | 7/2012 | Gelfand et al. | |
| 2012/0221087 A1 | 8/2012 | Parnis et al. | |
| 2013/138193 A1 | 5/2013 | Durand et al. | |
| 2013/0289678 A1 | 10/2013 | Clark et al. | |
| 2014/0018788 A1 | 1/2014 | Engelman et al. | |
| 2014/0364921 A1 | 12/2014 | Legay et al. | |
| 2014/0364923 A1 | 12/2014 | Legay et al. | |
| 2015/0202437 A1 | 7/2015 | Franke et al. | |
| 2015/0202441 A1 | 7/2015 | Franke et al. | |
| 2015/0202444 A1 | 7/2015 | Franke et al. | |

FOREIGN PATENT DOCUMENTS

| | | |
|---|---|---|
| CN | 101048194 A | 10/2007 |
| CN | 101657230 A | 2/2010 |
| CN | 101972513 A | 2/2011 |
| CN | 103372262 A | 10/2013 |
| CN | 106573139 A | 4/2017 |
| CN | 106573143 A | 4/2017 |
| CN | 106573144 A | 4/2017 |
| CN | 106573145 A | 4/2017 |
| EP | 3094369 B1 | 1/2018 |
| EP | 3094366 B1 | 6/2018 |
| JP | 2006508768 A | 3/2006 |
| JP | 2011502022 A | 1/2011 |
| JP | 2011502586 A | 1/2011 |
| JP | 2017502786 A | 1/2017 |
| JP | 2017502787 A | 1/2017 |
| KR | 20120126140 A | 11/2012 |
| KR | 1020120126140 A | 11/2012 |
| WO | WO-2007103324 A1 | 9/2007 |
| WO | WO-2009058258 A1 | 5/2009 |
| WO | WO-2009061813 A1 | 5/2009 |
| WO | WO-2010019481 A1 | 2/2010 |
| WO | WO-2012021583 A1 | 2/2012 |
| WO | WO-2013018083 A2 | 2/2013 |
| WO | WO-2015109015 A1 | 7/2015 |
| WO | WO-2015109018 A1 | 7/2015 |
| WO | WO-2015109023 A1 | 7/2015 |
| WO | WO-2015109024 A1 | 7/2015 |

OTHER PUBLICATIONS

Franke, Manfred, et al., "Selective Nerve Stimulation Using Presynaptic Terminal Depletion Block", U.S. Appl. No. 61/928,732, filed Jan. 17, 2014.

Franke, Manfred, et al., "Systems and Methods for Delivering Pulmonary Therapy", U.S. Appl. No. 61/928,714, filed Jan. 17, 2014.

Franke, Manfred, et al., "Systems and Methods for Selective Stimulation of Nerve Fibers in Carotid Sinus", U.S. Appl. No, 61/928,707, filed Jan. 17, 2014.

Kilgore, K L, et al., "Nerve conduction block utilising high-frequency alternating current", 14 pgs.

Mokelke, Eric A., et al., "System and Method for Mapping Baroreceptors", U.S. Appl. No. 61/836,431, filed Jun. 18, 2013.

msu.edu, "Mechanism of Action of Bronchodilator Drugs", Link: http://cvm.msu.edu./research/research-labs/equine-pulmonary-laboratory/respiratory-diseases/heaves/mechanism-of-action-of-bronchodilator-drugs.

Rattay, Frank, "Electrical Nerve Stimulation Theory, Experiments and Applications", 26 pgs.

"U.S. Appl. No. 14/597,112, Non Final Office Action dated Jan. 13, 2017", 10 pgs.

"U.S. Appl. No. 14/597,131, Advisory Action dated Nov. 4, 2016", 5 pgs.

"U.S. Appl. No. 14/597,131, Response filed Sep. 28, 2016 to Final Office Action dated Jul. 28, 2016", 12 pgs.

"U.S. Appl. No. 14/597,131, Response filed Dec. 28, 2016 to Final Office Action dated Jul. 28, 2016", 12 pgs.

(56) References Cited

OTHER PUBLICATIONS

"Australian Application Serial No. 2015206540, Office Action dated Nov. 7, 2016", 3 pgs.
"Australian Application Serial No. 2015206541, First Examiners Report dated Oct. 11, 2016", 3 pgs.
"U.S. Appl. No. 14/597,112, Response filed Apr. 13, 2017 to Non Final Office Action dated Jan. 13, 2017", 9 pgs.
"U.S. Appl. No. 14/597,131, Non Final Office Action dated Feb. 24, 2017", 16 pgs.
"U.S. Appl. No. 14/597,131, Response filed May 18, 2017 to Non Final Office Action dated Feb. 24, 2017", 24 pgs.
"Australian Application Serial No. 2015206540, Response filed Apr. 6, 2017 to Office Action dated Nov. 7, 2016", 12 pgs.
"European Application Serial No. 15701907.6, Response filed Mar. 24, 2017 to Communication Pursuant to Rules 161(1) and 162 EPC dated Sep. 22, 2016", 7 pgs.
"European Application Serial No. 15701908.4, Response filed Apr. 10, 2017 to Communication Pursuant to Rules 161(1) and 162 EPC dated Sep. 30, 2016", 7 pgs.
"European Application Serial No. 15701910.0, Response filed Apr. 3, 2017 to Communication Pursuant to Rules 161(1) and 162 EPC dated Oct. 5, 2016", 14 pgs.
"European Application Serial No. 15702608.9, Response filed Mar. 29, 2017 to Communication Pursuant to Rules 161(1) and 162 EPC dated Sep. 21, 2016", 9 pgs.
"U.S. Appl. No. 14/597,112, Advisory Action dated Oct. 20, 2017", 4 pgs.
"U.S. Appl. No. 14/597,112, Final Office Action dated Jul. 12, 2017", 10 pgs.
"U.S. Appl. No. 14/597,112, Pre-Appeal Brief Request filed Nov. 13, 2017", 5 pgs.
"U.S. Appl. No. 14/597,112, Response filed Sep. 12, 2017 to Final Office Action dated Jul. 12, 2017", 11 pgs.
"U.S. Appl. No. 14/597,131, Appeal Brief filed Mar. 16, 2018", 24 pgs.
"U.S. Appl. No. 14/597,131, Examiner Interview Summary dated Oct. 25, 2017", 4 pgs.
"U.S. Appl. No. 14/597,131, Final Office Action dated Aug. 23, 2017", 18 pgs.
"U.S. Appl. No. 14/597,131, Pre-Appeal Brief Request filed Nov. 24, 2017", 5 pgs.
"U.S. Appl. No. 14/597,137, Advisory Action dated Jan. 3, 2018", 3 pgs.
"U.S. Appl. No. 14/597,137, Final Office Action dated Oct. 23, 2017", 13 pgs.
"U.S. Appl. No. 14/597,137, Non Final Office Action dated Mar. 26, 2018", 10 pgs.
"U.S. Appl. No. 14/597,137, Non Final Office Action dated Jun. 6, 2017", 16 pgs.
"U.S. Appl. No. 14/597,137, Response filed Sep. 6, 2017 to Non Final Office Action dated Jun. 6, 2017", 12 pgs.
"U.S. Appl. No. 14/597,137, Response filed Dec. 13, 2017 to Final Office Action dated Oct. 23, 2017", 15 pgs.
"Australian Application Serial No. 2015206541, Response filed Jul. 27, 2017 to First Examiners Report dated Oct. 11, 2016", 15 pgs.
"Japanese Application Serial No. 2016-547078, Office Action dated Jul. 4, 2017", w/ English translation, 13 pgs.
"Japanese Application Serial No. 2016-547078, Response filed Dec. 27, 2017 to Office Action dated Jul. 4, 2017", w/ claims in English, 11 pgs.
"Japanese Application Serial No. 2016-547080, Office Action dated Jun. 27, 2017", w/ English translation, 11 pgs.
"Japanese Application Serial No. 2016-547080, Response filed Oct. 13, 2017 to Office Action dated Jun. 27, 2017", w/ claims in English, 10 pgs.
"U.S. Appl. No. 14/597,131, Final Office Action dated Jul. 28, 2016", 14 pgs.
"U.S. Appl. No. 14/597,131, Non Final Office Action dated Mar. 28, 2016", 16 pgs.
"U.S. Appl. No. 14/597,131, Response filed Jun. 28, 2016 to Non Final Office Action dated Mar. 28, 2016", 15 pgs.
"International Application Serial No. PCT/US2015/011458, International Preliminary Report on Patentability dated Jul. 28, 2016", 7 pgs.
"International Application Serial No. PCT/US2015/011458, International Search Report dated Mar. 31, 2015", 3 pgs.
"International Application Serial No. PCT/US2015/011458, Written Opinion dated Mar. 31, 2015", 5 pgs.
"International Application Serial No. PCT/US2015/011461, International Preliminary Report on Patentability dated Jul. 28, 2016", 8 pgs.
"International Application Serial No. PCT/US2015/011461, International Search Report dated Mar. 27, 2015", 6 pgs.
"International Application Serial No. PCT/US2015/011461, Written Opinion dated Mar. 27, 2015", 7 pgs.
"International Application Serial No. PCT/US2015/011467, International Preliminary Report on Patentability dated Jul. 28, 2016", 10 pgs.
"International Application Serial No. PCT/US2015/011467, International Search Report dated Mar. 26, 2015", 5 pgs.
"International Application Serial No. PCT/US2015/011467, Written Opinion dated Mar. 26, 2015", 8 pgs.
"International Application Serial No. PCT/US2015/011468, International Preliminary Report on Patentability dated Jul. 28, 2016", 9 pgs.
"International Application Serial No. PCT/US2015/011468, International Search Report dated Mar. 30, 2015", 5 pgs.
"International Application Serial No. PCT/US2015/011468, Written Opinion dated Mar. 30, 2015", 7 pgs.
Bhakta, Bipin B, et al., "Management of spasticity in stroke", British Medical Bulletin, 56 (No. 2), (2000), 476-485.
Canning, Brendan J., et al., "Evidence That Distinct Neural Pathways Mediate Parasympathetic Contractions and Relaxations of Guinea-Pig Trachealis", Journal of Physiology (1993), 471, (1993), 25-40.
Canning, Brendan J., "Reflex regulation of airway smooth muscle tone", J Appl Physiol 101, (2006), 971-985.
Chang, C. C., et al., "Mechanisms of the inhibition by neostigmine of tetanic contraction in the mouse diaphragm", Br. J. Pharmac. 87, (1986), 757-762.
Coleridge, H M, et al., "Characteristics of C Fibre Baroreceptors in the Carotid Sinus of Dogs", J. Physiol. (1987), 394, (1987), 291-313.
Fisher, Karen M., et al., "Blocking central pathways in the primate motor system using high-frequency sinusoidal current", J Neurophysiol 113(5): 1670-1680, Mar. 1, 2015.
Franke, Manfred, et al., "Translating Electric KHFAC and DC Nerve Block from Research to Application", PhD Thesis, Case Western Reserve University, (May 2014), 199 pgs.
Gosens, Reinoud, et al., "Muscarinic receptor signaling in the pathophysiology of asthma and COPD", Respiratory Research 2006, 7:73, (2006), 1-15.
Hoffman, Thomas J., et al., "Inhibition of Histamine-Induced Bronchoconstriction in Guinea Pig and Swine by Pulsed Electrical Vagus Nerve Stimulation", Neuromodulation vol. 12; No. 4, (2009), 261-269.
Hoffman, Thomas J., et al., "Low Voltage Vagal Nerve Stimulation Reduces Bronchoconstriction in Guinea Pigs Through Catecholamine Release", Neuromodulation. 2012 ; 15(6), (2012), 527-536.
Ishii, Koji, et al., "Effects of Neostigmine on Bronchoconstriction With Continuous Electrical Stimulation in Rats", Journal of Anesthesia, Springer-Verlag, TO, vol. 26, No. 1, (Nov. 1, 2011), 80-84.
Kilgore, K L, et al., "Nerve conduction block utilising high-frequency alternating current", Medical & Biological Engineering & Computing 2004, vol. 42, 14 pgs.
Kilgore, Kevin, et al., "Combined Direct Current and High Frequency Nerve Block for Elimination of the Onset Response", 31st Annual International Conference of the IEEE EMBS, Minneapolis, Minnesota, USA, Sep. 2-6, 2009, (2009), 197-199.
Kilgore, Kevin L, et al., "Reversible Nerve Conduction Block Using Kilohertz Frequency Alternating Current", Neuromodulation: Technology at the Neural Interface, (2013), 13 pgs.

(56) References Cited

OTHER PUBLICATIONS

Krzyzaniak, Michael J., et al., "Efferent vagal nerve stimulation attenuates acute lung injury following burn: The importance of the gut-lung axis", Surgery; 150(3):, (Sep. 2011), 379-389.

Lopez, Nicole E, et al., "Vagal Nerve Stimulation Blocks Peritoneal Macrophage Inflammatory Responsiveness after Severe Burn Injury", Shock. Aug. 2012 ; 38(3):, (Aug. 2012), 294-300.

msu.edu, "Mechanism of Action of Bronchodilator Drugs", Link: http://cvm.msu.edu/research/research-labs/equine-pulmonary-laboratory/respiratory-diseases/heaves/mechanism-of-action-of-bronchodilator-drugs, Jan. 15, 2015.

Paton, Julian, et al., "The Carotid Body as a Therapeutic Target for the Treatment of Sympathetically Mediated Diseases", Hypertension. 2013; 61, (2013), 5-13.

Rattay, Frank, "Electrical Nerve Stimulation Theory, Experiments and Applications", (1990) 26 pgs.

Seagard, J L, et al., "Firing characteristics of single-fiber carotid sinus baroreceptors.", Circulation Research Journal of The American Heart Association; 66:1499-1509, (1990), 12 pgs.

Sepulveda, P., et al., "Treatment of asthmatic bronchoconstriction by percutaneous low voltage nerve stimulation: case report", The Internet Journal of Asthma, Allergy and Immunology, vol. 7 No. 2, (2008).

Solomonow, M., et al., "Control of Muscle Contractile Force Through Indirect High-Frequency Stimulation", Amer. Journal of Physical Med.; vol. 62 No. 2, (1983), 71-82.

Stretton, C, et al., "Sensory Nerve Depletion Potentiates Inhibitory Non-Adrenergic, Non-Cholinergic Nerves in Guinea-Pig Airways", European Journal of Pharmacology, Elsevier Science, NL, vol. 184, No. 2-3, (Aug. 10, 1990), 333-337.

Strickland, Michael, et al., "Carotid Chemoreceptor Modulation of Regional Blood Flow Distribution During Exercise in Health and Chronic Heart Failure", Circulation Research. 100., (2007), 1371-1378.

Tkacova, Ruzena, "Systemic Inflammation in Chronic Obstructive Pulmonary Disease:May Adipose Tissue Play a Role? Review of the Literature and Future Perspectives", Mediators of Inflammation; vol. 2010, Article ID 585989, (2010), 1-12.

Undem, Bradley J., et al., "Autonomic Neural Control of Intrathoracic Airways", American Physiological Society; Comprehensive Physiology; 2, (2012), 1241-1267.

Undem, Bradley J., et al., "The Role of Vagal Afferent Nerves in Chronic Obstructive Pulmonary Disease", Proceedings of the American Thoracic Society vol. 2, (2005), 355-360.

Van Den Berge, M., et al., "Clinical and inflammatory determinants of bronchial hyperresponsiveness in COPD", Eur Respir J; 40:, (2012), 1098-1105.

Wedensky, N.E., "Die Erregung, Hemmung und Narkose (The excitation, inhibition and Narkose)", Archiv für die gesamte Physiologie des Menschen und der Tiere, (1903) 100: p. 1-144 (With Machine Translation).

Wedensky, N.E., "Ueber einige Beziehungen zwischen der Reizstarke und der Tetanushohe bei indirecter Reizung Over some relations between the attraction strength and the Tetanushöhe when indireeter provoking", Archiv für die gesamte Physiologie des Menschen und der Tiere of Dr. E.F.W. Pflüger, 37: p. 69-72, Dec. 1885 (With Machine Translation).

Wine, Jeffrey J., et al., "Parasympathetic control of airway submucosal glands: Central reflexes and the airway intrinsic nervous system", Autonomic Neuroscience: Basic and Clinical 133, (2007), 35-54.

Wodlinger, Brian, et al., "Block of Peripheral Pain Response by High-Frequency Sinusoidal Stimulation", Neuromodulation; 16, (2013), 312-317.

Zhang, Yong, et al., "Ganglionated Plexi Ablation for Atrial Fibrillation", Basic Research and Clinical Applications, Prof. Jong-Il Choi (Ed.), ISBN: 978-953-307-399-6, InTech,, Available from: http://www.intechopen.com/books/atrial-fibrillation-basic-research-andclinical-applications/ganglionated-plexi-ablation-for-atrial-fibrillation, (2012), 239-255.

"U.S. Appl. No. 14/597,137, Notice of Allowance dated Sep. 25, 2018", 10 pgs.

"U.S. Appl. No. 14/597,137, Respone filed Jul. 26, 2018 to Non Final Office Action dated Mar. 26, 2018", 13 pgs.

"Chinese Application Serial No. 201580014596.3, Office Action dated Aug. 8, 2018", W/ English Translation, 17 pgs.

"Chinese Application Serial No. 201580014597.8, Office Action dated Jul. 3, 2018", w/ English translation, 11 pgs.

"Chinese Application Serial No. 201580014615.2, Office Action dated Jun. 28, 2018", W/ English summary, no translation sent, only brief summary from agent letter, 10 pgs.

"Chinese Application Serial No. 201580014616.7, Office Action dated Jun. 28, 2018", w/ English translation, 21 pgs.

"Japanese Application Serial No. 2016-547078, Office Action dated May 29, 2018", w/ English translation, 4 pgs.

"Japanese Application Serial No. 2016-547080, Office Action dated Apr. 3, 2018", w/ English translation, 9 pgs.

"Japanese Application Serial No. 2016-547080, Response filed Jul. 30, 2018 to Office Action dated Apr. 3, 2018", w/ English claims, 10 pgs.

"Chinese Application Serial No. 201580014596.3, Response filed Feb. 22, 2019 to Office Action dated Aug. 8, 2018", w/ English claims, 17 pgs.

"Chinese Application Serial No. 201580014597.8, Response filed Nov. 16, 2018 to Office Action dated Jul. 3, 2018", w/ English claims, 21 pgs.

"Chinese Application Serial No. 201580014615.2, Response filed Nov. 13, 2018 to Office Action dated Jun. 28, 2018", w/ English claims, 15 pgs.

"Chinese Application Serial No. 201580014616.7, Response filed Nov. 13, 2018 to Office Action dated Jun. 28, 2018", w/ English claims, 17 pgs.

"European Application Serial No. 15702608.9, Communication Pursuant to Article 94(3) EPC dated Dec. 20, 2018", 4 pgs.

"Japanese Application Serial No. 2016-547078, Response filed Aug. 17, 2018 to Office Action dated May 29, 2018", w/ English claims, claims were not amended in response, current claims from previous response filed included in attachment, 4 pgs.

"Japanese Application Serial No. 2016-547080, Office Action dated Dec. 25, 2018", w/ English translation, 12 pgs.

\* cited by examiner

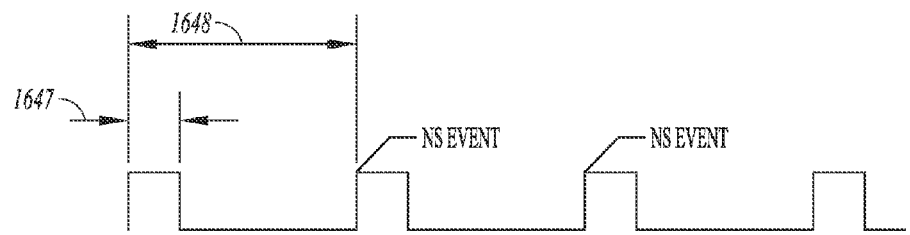
FIG. 16
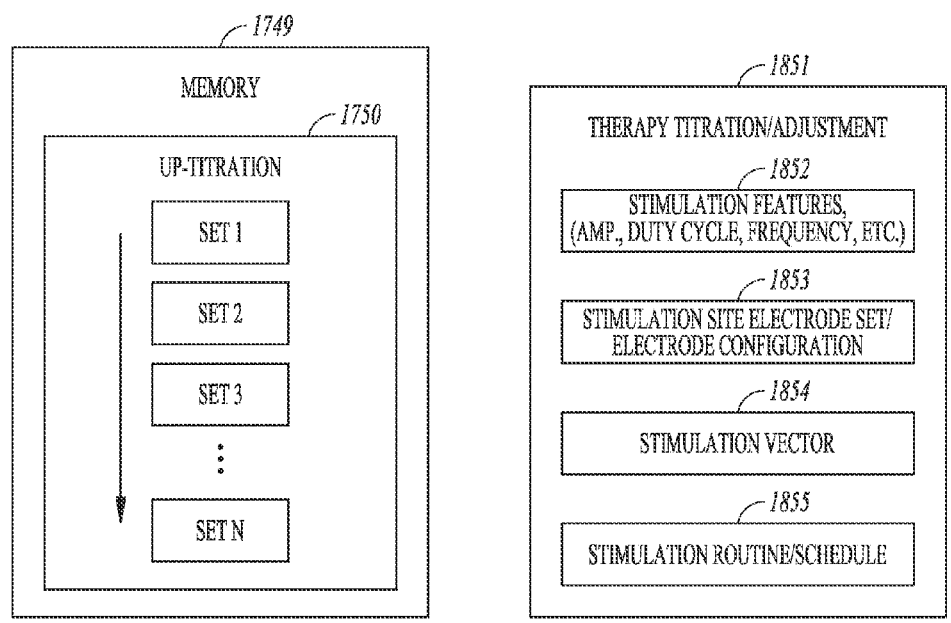
FIG. 17
FIG. 18

SELECTIVE NERVE STIMULATION USING PRESYNAPTIC TERMINAL DEPLETION BLOCK

CLAIM OF PRIORITY

This application claims the benefit of priority under 35 U.S.C. § 119(e) of U.S. Provisional Patent Application Ser. No. 61/928,732, filed on Jan. 17, 2014, which is herein incorporated by reference in its entirety.

CROSS REFERENCE TO RELATED APPLICATIONS

The following commonly-assigned U.S. patent application are related, are all filed on the same date as the present application, and are all herein incorporated by reference in their entirety: "Systems and Methods for Selective Stimulation of Nerve Fibers in Carotid Sinus," Ser. No. 61/928,707 filed on Jan. 17, 2014; "Systems and Methods for Delivering Pulmonary Therapy," Ser. No. 61/928,714 filed on Jan. 17, 2014; and "Depletion Block To Block Nerve Communication," Ser. No. 61/928,725 filed on Jan. 17, 2014.

TECHNICAL FIELD

This document relates generally to medical devices, and more particularly, to systems, devices and methods for delivering selective nerve stimulation.

BACKGROUND

Neural stimulation has been proposed as a therapy for a number of conditions. By way of example, neural stimulation may be delivered to modulate the autonomic system, which may be referred to as an autonomic modulation therapy (AMT). Examples of AMT include therapies for respiratory problems such as sleep disordered breathing, blood pressure control such as to treat hypertension, cardiac rhythm management, myocardial infarction and ischemia, heart failure (HF), and modulation of the cholinergic anti-inflammatory pathway. For example, therapies to treat epilepsy, depression, pain, migraines, eating disorders and obesity, and movement disorders may include stimulation of a vagus nerve.

Some neural targets are complex structures with different types of nerve fibers that may innervate different portions of the body. Indiscriminate stimulation of such complex structures may provide a desirable effect, but may also provide an undesired side effect. For example, the cervical vagus nerve is a combined nerve with different sized fibers. A recurrent laryngeal nerve branches off from the cervical vagus and innervates the muscle around the larynx. The vagus nerve continues to descend below the laryngeal nerve branch to innervate other portions of the body including the heart, lungs, liver, stomach, intestines, bladder and kidneys. Therapies, such as a heart failure therapy, that stimulate the cervical vagus nerve have been proposed. It may desirable to stimulate the cervical vagus nerve in a manner that activates the fibers that innervate the heart without activating some other fibers in the cervical vagus nerve so as to avoid unwanted physiologic responses to the stimulation.

SUMMARY

Various embodiments described may relate to methods and systems that can deliver neural stimulation and depletion block stimulation. The neural stimulation may be applied to cause action potentials in some axons, and the depletion block stimulation may be applied to block action potentials in at least some of these from being communicated across a synaptic cleft.

An example of a system may include a stimulator and at least one controller. The stimulator may be configured to deliver nerve stimulation to capture a first set of axons in a nerve and to deliver depletion block stimulation to capture a second set of axons in the nerve, where the second set of axons is a subset of the first set of axons. The depletion block stimulation may include a series of pulses at a depletion pulse frequency within a range between about 100 Hz to about 1 kHz (e.g. 100 Hz to 1000 Hz or frequencies near that range to provide the depletion block), and the nerve stimulation may include a series of pulses at a stimulation pulse frequency within a range of about 0.25 Hz to about 50 Hz. The at least one controller may be configured to communicate with the stimulator and control the depletion block stimulation and the nerve stimulation. At least a portion of the nerve stimulation and at least a portion of the depletion block stimulation may be delivered to be effective in providing a nerve block while delivering nerve stimulation.

An example of a method may include delivering stimulation to a nerve having a plurality of axons. Delivering stimulation may include delivering nerve stimulation configured to capture a first set of axons in the nerve. Delivering nerve stimulation may include delivering a series of electrical pulses at a stimulation pulse frequency where the stimulation pulse frequency is between the range of about 0.25 Hz and about 50 Hz, where the delivered nerve stimulation is capable of inducing action potentials in the first set of axons. Delivering stimulation may include delivering a presynaptic depletion block stimulation configured to capture a second set of axons in the nerve. The second set may be a subset of the first set. Delivering the presynaptic depletion block stimulation may include delivering a series of electrical pulses at a depletion pulse frequency. The depletion pulse frequency may be within a range between about 100 Hz to about 1 kHz. At least a portion of the nerve stimulation and at least a portion of the depletion block stimulation are delivered to be effective in providing a nerve block while delivering nerve stimulation.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 16 illustrates, by way of example, a representation of intermittent neural stimulation (INS).

FIG. 17 illustrates a memory which may be incorporated in the controller in FIG. 14 or FIG. 15, according to various embodiments, and which may include instructions, operable on by the stimulation control circuitry, for controlling an up-titration routine.

FIG. 18 illustrates an embodiment of a therapy titration module, which may be part of the titration control module in FIG. 15.

DETAILED DESCRIPTION

Figure 1:
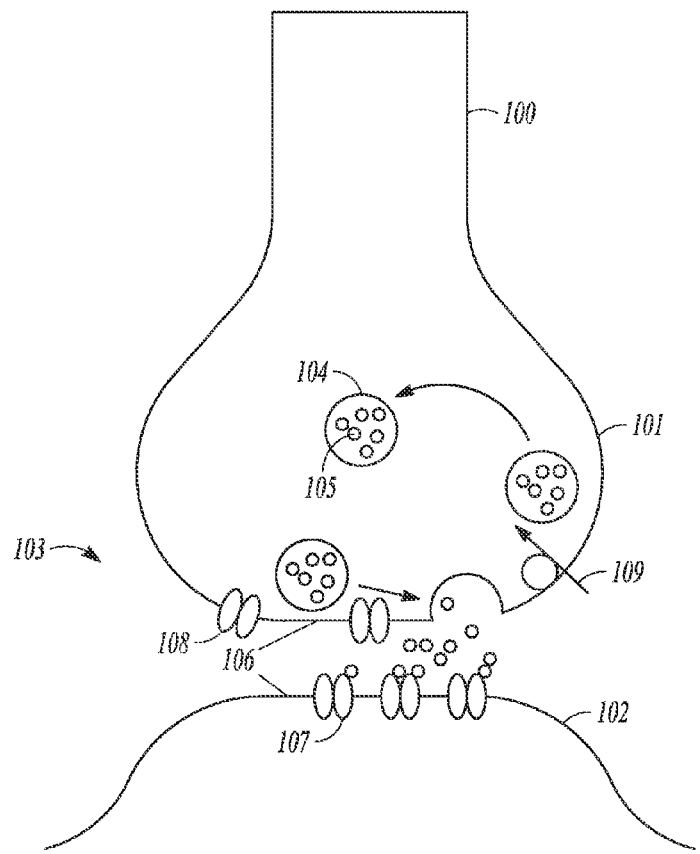
FIG. 1 illustrates neural activity at a synapse between a nerve and another membrane.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Nerve fibers, also referred to as axons, are projections from nerve cells. A nerve fiber connects a nerve cell to another nerve cell or to muscle or to gland cells at synapses. Synapses are structures that permit nerve cells to pass an electrical or chemical signal to other cells. Nerve fibers includes A fibers, B fibers, and C fibers. A fibers are the largest and, generally, the first captured as stimulation amplitude increases. A fibers can be sensory fibers (afferent) or motor fibers (efferent) that innervate muscle tissue. For example, stimulation of the vagus nerve in the cervical region may excite laryngeal muscle fibers which causing laryngeal activation which may be used as a marker for capture of the vagus nerve. B fibers are smaller and next to be captured when increasing current amplitude. These are typically efferent parasympathetic and sympathetic fibers. These B fibers may be a target for an autonomic neural stimulation therapy. C fibers are the smallest and associated with pain and other sensory information.

It has been observed that thicker nerve fibers are generally activated before thinner nerve fibers. Thick nerve fibers have longer sections of myelin sheaths between the nodes of Ranvier where the depolarization occurs and thus the change in electric field they experience is greater. It is currently believed that the vagus nerve includes the fiber types and sizes illustrated in Table 1, and it is further believed that the majority of the fibers are C fibers.

TABLE 1

Vagal Nerve Fibers

| Fibers | Origin | Size (um) | Conduction Velocity (m/s) | Innervation |
| --- | --- | --- | --- | --- |
| Aα | Motor | 13-20 | 80-120 | Larynx |
| Aγ | Motor | 5-8 | 4-24 | |
| Aα | Sensory | 13-20 | 80-120 | All organs |
| Aβ | Sensory | 6-12 | 33-75 | larynx and airways |
| Aδ | Sensory | 1-5 | 3-30 | lungs, heart |
| B (pre-g) | Efferent | 1-5 | 3-15 | stomach, pancreas |
| C (pos-g) | Efferent | 0.2-1.5 | 0.5-2 | bladder |
| C | Sensory | 0.2-1.5 | 0.5-2 | |

Some proposed autonomic neural stimulation therapies attempt to capture as many nerve fibers in the vagus nerve as possible by titrating amplitude up as high as tolerable. In general terms vagal stimulation may first capture A motor and large sensory nerves fibers, then small sensory and B parasympathetic nerve fibers. This order is a general order because fibers that are closer to the electrodes experience a stronger electric field and are activated before fibers that are further away, and further these fiber types overlap in their size. The fibers that drive heart rate down are the smallest B efferent parasympathetic fibers. These B efferent parasympathetic fibers are the smallest of the myelinated fibers, as the C fibers are unmyelinated. Neural stimulation that causes a heart rate response indicates that the B efferent parasympathetic fibers have been captured and that the other larger fiber types are also being captured.

FIG. 1 illustrates neural activity at a synapse between a nerve and another membrane. An action potential propagates electrically down nerve axon 100 until it reaches a nerve ending, which may be referred to as a presynaptic terminal 101. The presynaptic terminal communicates with a postsynaptic membrane 102 of a target cell. The target cell may be another nerve or a muscle or gland. This membrane-to-membrane junction of the presynaptic terminal and the target cell is referred to as a synapse 103. A type of synapse is an electrical synaptic junction where the presynaptic terminal electrically communicates with the postsynaptic membrane using ions or small molecules that pass through channels from one cell to the next. Another type of synapse is a chemical synaptic junction, where neurotransmitters are used to transmit between cells. The presynaptic area 101 has a large number of synaptic vesicles 104 that contain neurotransmitter chemicals 105. Action potentials that propagate to the presynaptic terminal 101 drive a chemical reaction in the presynaptic terminal that releases neurotransmitters from synaptic vesicles within the terminal into the extracellular space. This extracellular space may be referred to as a synaptic cleft 106. The neurotransmitters cross the synaptic cleft between the presynaptic and postsynaptic terminals. The neurotransmitters start a chain of reaction in receptors 107 of either the post-synaptic membrane 102 (another neuronal cell) or the muscle cells (neuromuscular junction) that trigger either the firing of an action potential in the post-synaptic neuron or the muscular contraction if the synapse ends in a neuromuscular junction. For example, where the target cell is a muscle and the synapse is a neuromuscular junction, the neurotransmitter acetylcholine (Ach) causes a rapid contraction of the target muscle cell. At a neuromuscular junction, the action potential travels to the neuromuscular synaptic junction, causing calcium ions to flow through voltage-gated calcium channels 108 which release Ach from the presynaptic terminal into the extracellular space. Postsynaptic receptors in the membrane of the target muscle cell receive the Ach. The presynaptic terminal has a neurotransmitter re-uptake pump 109 that replenishes the presynaptic terminal with synaptic vesicles of neurotransmitters.

The present inventors have observed that continual communication across this synaptic cleft 106 appears to require a minimal amount of time between action potentials in the nerve, having observed that post-synaptic receptors do not trigger action potentials if the pre-synaptic action potentials arrive close to each other. Higher stimulation frequencies will generate more stimulation pulses in a given period of time, and may generate more corresponding action potentials in the nerve during the period of time. For example, a neural stimulation signal may be within a range from about 0.25 Hz to 50 Hz, or may be within a range of about 2 Hz to about 20 Hz, or may be about 20 Hz. At higher frequencies (e.g. about 100 Hz to about 1 kHz), it was observed that the presynaptic terminal was unable to communicate across the synaptic cleft even though action potentials continued to propagate through the axon. This inability of the presynaptic terminal to communicate may be referred to as a depletion block. The frequencies used to obtain this depletion block are lower than the high frequency (greater than 1 kHz) AC nerve block that would block action potentials from propagating down the nerve. At frequencies higher than 1 kHz, for example, the stimulation blocks the nerve from conducting the action potentials. In contrast, the depletion block is delivered at frequencies below 1 kHz and thus does not stop the action potentials from propagating down the nerve to the presynaptic terminal, but rather depletes the presynaptic terminal so it is no longer able to communicate across the synaptic cleft to receptors of another cell.

Figure 2:
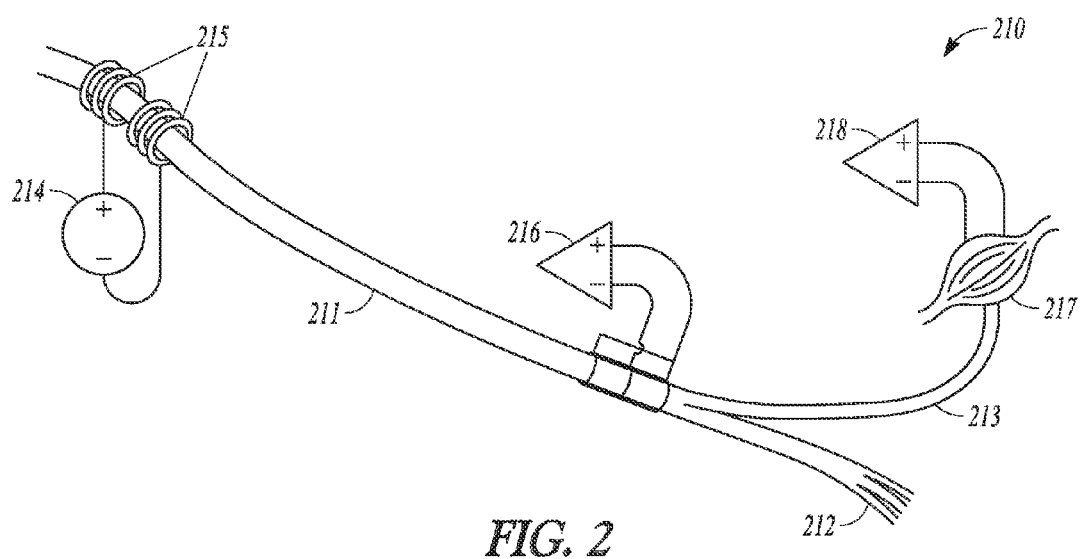
FIG. 2 illustrates an experimental setup used to observe a presynaptic terminal depletion block.

FIG. 2 illustrates an experimental setup 210 used to observe a presynaptic terminal depletion block. A cervical vagus nerve 211 branches into the thoracic branch 212 and the recurrent laryngeal nerve 213. The illustrated experimental setup was used to stimulate the cervical vagus nerve 213 using a current source 214 and helical electrodes 215 in a bipolar arrangement, to monitor neural activity before the cervical vagus nerve 211 branches into the recurrent laryngeal nerve branch 213 and the thoracic branch 212 using an electroneurography (ENG) monitor 216, and to monitor vibration of the laryngeal muscles 217 using an electromyography (EMG) monitor 218. This set up was used to observe that action potentials from depletion block stimulation were still sensed by the ENG but laryngeal vibrations were not sensed by the EMG 218. Thus, it could be concluded that the depletion block stimulation blocked the ability of the presynaptic terminal to communicate across the synaptic cleft.

Figure 3:
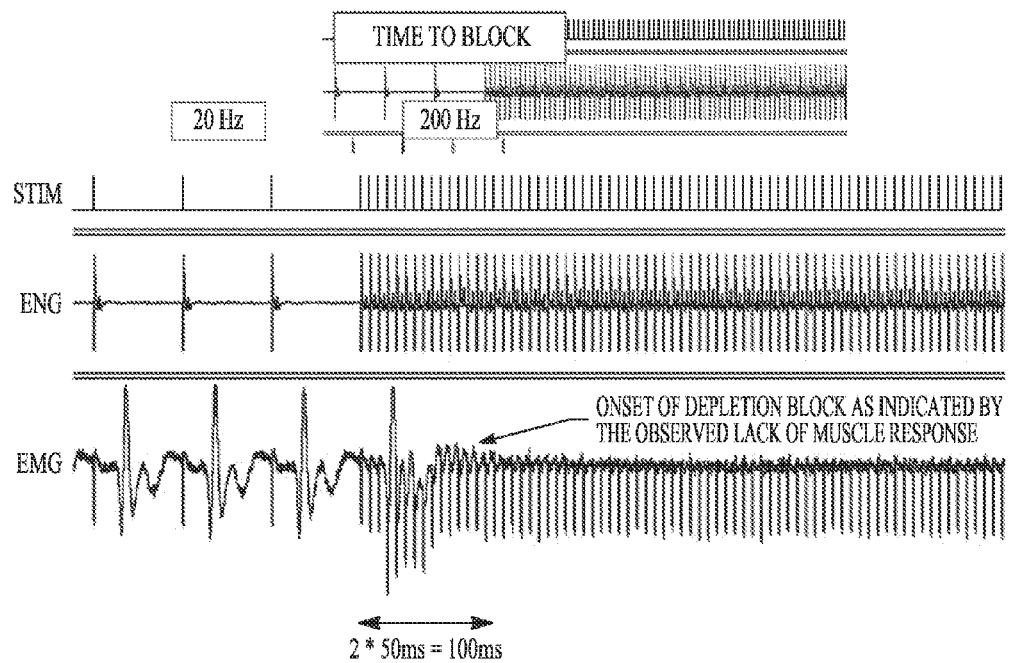
FIG. 3 illustrates the observed relationship between the stimulus signal and the recorded ENG and EMG signals when the stimulus changes from 20 Hz to 200 Hz, and also includes the observed time to deplete the presynaptic terminal and block the synaptic junction.

FIG. 3 illustrates the observed relationship between the stimulus signal and the recorded ENG and EMG signals when the stimulus changes from 20 Hz to 200 Hz, and also includes the observed time to deplete the presynaptic terminal and block the synaptic junction. During the 20 Hz stimulation, both the ENG and EMG signals follow the stimulus signal. The high peaks in both ENG and EMG signals reflect the stimulation artifact. However, during the 200 Hz stimulation, the ENG response is still present after the stimulus signal but the EMG signal quickly subsides after an onset response of about 100 ms. After a brief transitional period after the stimulus changes to 200 Hz, only the artifact from charge-balancing is seen in the EMG waveform. Thus, the axons in the nerve continue to be active by propagating action potentials, but the communication across the synaptic cleft is reduced or stopped after the presynaptic terminal has been depleted from its ability to communicate across the synaptic cleft. As illustrated, this synaptic junction block occurs very quickly (e.g. 50 to 100 ms after the 200 Hz signal is applied), as soon as the propagated pulses received at the presynaptic terminal deplete the presynaptic terminal from its ability to communicate. It does not appear that the physiological reuptake process that restores neurotransmitters and/or calcium in the presynaptic terminal can keep up with the transmission of the neurotransmitters from the 200 Hz stimulation.

Figure 4:
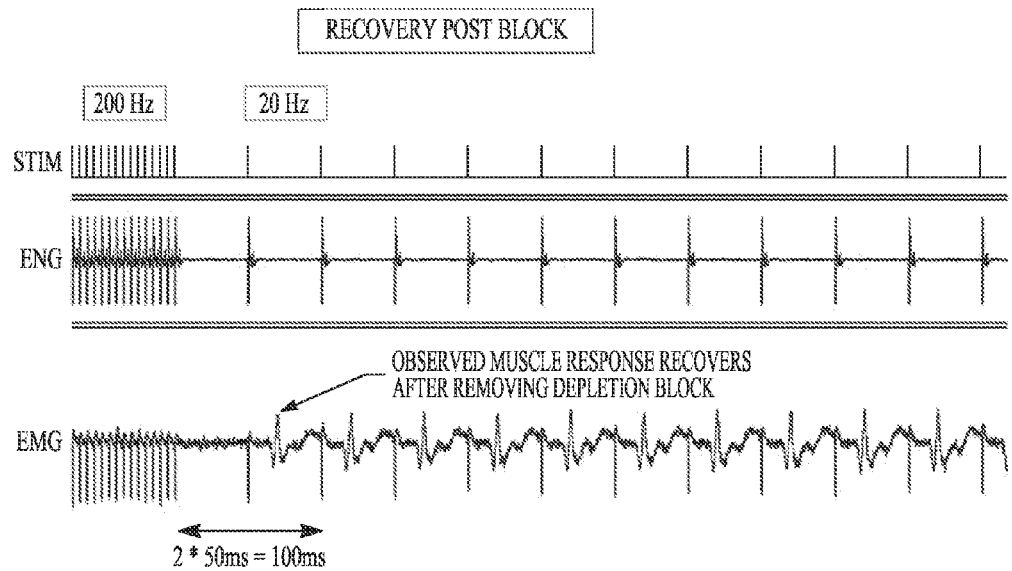
FIG. 4 illustrates the relationship between the stimulus signal and the recorded ENG and EMG signals when the stimulus changes from 200 Hz to 20 Hz.

FIG. 4 illustrates the relationship between the stimulus signal and the recorded ENG and EMG signals when the stimulus changes from 200 Hz to 20 Hz. The synaptic junction block occurs when the stimulus is delivered at 200 Hz. During this time, the ENG is still present following the stimulus artifact signal but the EMG response is not present. This indicates that the stimulus is capturing the nerve and causing action potentials to propagate through the axon. Every pulse in the stimulation causes a respective action potential in the nerve fiber. However, the laryngeal muscle is not stimulated because of the presynaptic terminal depletion that causes the synaptic junction block. The 200 action potentials per second deplete the ability of the presynaptic terminal to communicate across the synaptic cleft. When the stimulus changes from 200 Hz to 20 Hz, however, the ENG response continues to be present following the stimulus pulse as every pulse in the stimulation causes a respective action potential in the nerve fiber. The EMG reappears right after the stimulus pulse just after a brief transitional period after the stimulation frequency changes to 20 Hz. The ability of the presynaptic terminal to communicate across the synaptic cleft is not depleted by 20 pulses per second. Thus, as illustrated, the synaptic junction block can be removed very quickly (e.g. 50 ms to 100 ms after the signal changes from 200 Hz to 20 Hz signal), which is believed to reflect the physiological response time for restoring neurotransmitters and/or calcium in the presynaptic terminal.

As illustrated in Table 2, it was observed that certain frequencies turned the depletion block of the synaptic junction on/off more quickly than other frequencies. Data suggest that frequencies greater than about 200 Hz provide a fast depletion block, whereas frequencies between about 100 to about 150 Hz provides slower depletion blocks. Frequencies below 100 Hz tend not be effective to provide the depletion block, as those frequencies do not exceed the ability of the presynaptic terminal to restore its ability to communicate from the presynaptic terminal across the synaptic cleft to the target cell. In a neural muscular junction, for example, frequencies less than about 100 Hz cause tetanic contraction; frequencies between about 100 to about 150 Hz causes a 90% depletion block in about 10 seconds to 4 seconds; a frequency between about 200 Hz to 1000 Hz causes a 90% depletion block; and a frequency is greater than 1 kHz starts to enter into nerve conduction block where the stimulation arrests the actions potentials from propagating down the nerve.

TABLE 2

| | Freq (Hz) | Time to 90% Block (sec) | | Percentage of unblocked EMG (%) | |
|---|---|---|---|---|---|
| | | mean | stdev | mean | stdev |
| Activation | 40[1] | — | — | 110 | 13.18 |
| | 70[1] | — | — | 39 | 8.42 |
| Slow Block | 100*,[2] | 10.74 | 2.2 | 8.2 | 3.77 |
| | 130[1] | 9.33 | 0.55 | 4.38 | 1.06 |
| | 150[2] | 4.43 | 2.59 | 3.88 | 1.13 |
| Fast Block | 200[2] | 0.53 | 0.16 | 2.25 | 1.04 |
| | 260[1] | 0.16 | 0.05 | 0.75 | 0.89 |
| | 300[2] | 0.13 | 0.05 | 1.13 | 1.13 |
| | 400[1] | 0.14 | 0.05 | 0.63 | 0.74 |

Randomized study; n = 8 (100 Hz: n = 5), data from 2 * N = 1

Figure 5A:
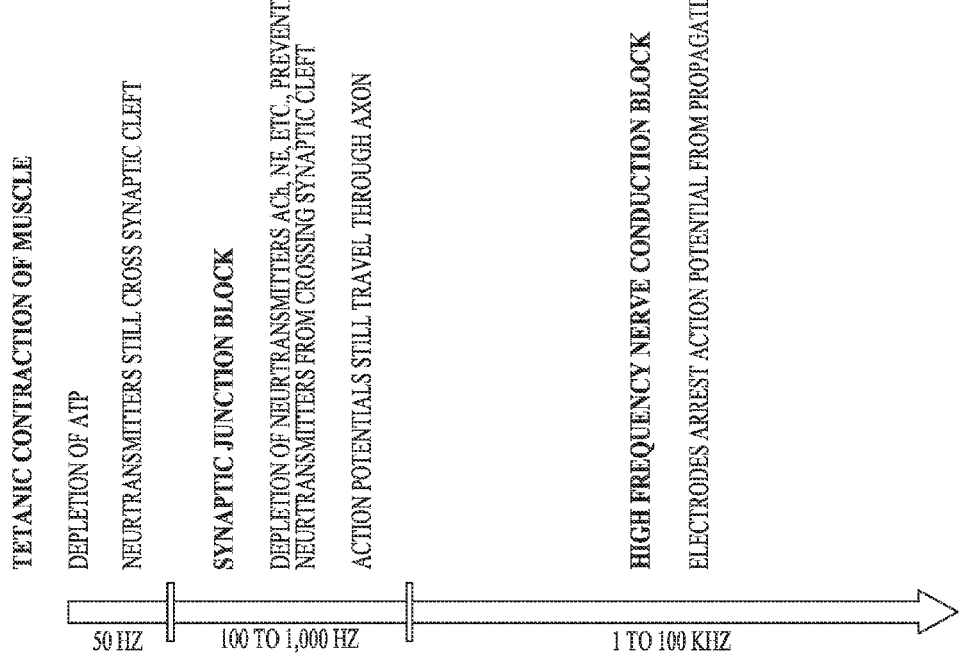
FIGS. 5A and 5B illustrate the response of a neural muscular junction to different stimulation frequencies.

FIG. 5A illustrates the response of a neural muscular junction to different stimulation frequencies. The neural muscular junction is a type of synaptic junction where an axon in a nerve communicates with muscle. Stimulation of axons within a range generally below 100 Hz (e.g. about 50 Hz) may cause a tetanic contraction of the muscle. Eventually, the muscle may fatigue and no longer respond to additional stimulation. The presynaptic terminal is depleted from its ability to communicate across the synaptic cleft at stimulation frequencies within a range from about 100 Hz to about 1 kHz. This frequency of the stimulation signal is outside of the ability of the physiological system to trigger the muscular contraction, as the frequency may cause the action potentials to arrive faster than the neurotransmitters and/or calcium can be replenished for subsequent action potentials in the stimulation. The observed block is attributable to a depletion of the junction but not fatigue of the muscle. Thus, a benefit of the depletion block applied to neural muscular junctions is that the depletion block does not cause muscle fatigue or tetanic contraction. The neuromuscular depletion block is quickly reversible by stopping stimulation.

Figure 5B:
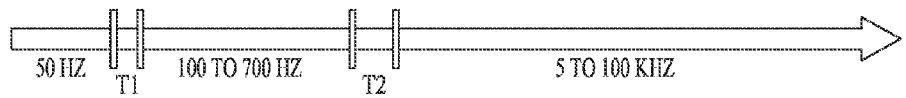

It is noted that FIG. 5A is a simple illustration of frequency ranges, and that these ranges may vary for different applications. FIG. 5B provides another illustration of a response of a neural muscular junction to different stimulation frequencies. FIG. 5B illustrates a transition period T1 between the activation and depletion block ranges. Transition period T1 may depend on the transmitter and the synaptic end-organ, and may range from about 70 to 130 Hz. FIG. 5B also illustrates a transition period T2 between the depletion block and conduction block ranges that may provide a combined depletion and conduction block.

Some characterizations of depletion block, combined depletion and conduction block, and high frequency kHz conduction blocks are provide below. For example, a depletion block has a lower frequency and thus lower power requirements, has a relatively fast block (<100 ms) and a relatively fast recovery (<100 ms over 50% and 10 seconds 100%). For example, a combined depletion and conduction block (e.g. around 1 kHz) may block slow fibers extremely fast due to conduction block, may be initiated with a high kHz frequency and then lowered to keep the block at lower frequencies, may block slower fibers in less than 7 ms, and may have a faster recovery than the higher frequency kHz blocks. For example, a high frequency kHz conduction block is fast (e.g. on: <7 ms an off: <10 ms), but is more energy intensive due to higher frequencies and current requirements.

For example, a kHz conduction block may be observed with a lower boundary of about 1 kHz to 5 kHz rather than the simply illustrated 1 kHz. Additionally, the upper boundary of a depletion block may be about 2 kHz rather than the simply illustrated 1 kHz. Further, the frequencies for which stimulation transitions from depletion to conduction depends on the nerve fibers and end plate. Fast a-fibers have higher conduction and firing rates, so they will not necessarily block at 1 kHz, and slower fibers will block at lower frequencies (e.g. 600 Hz). Thus, there may be a nerve stimulation frequency band within which most fibers can be activated, a depletion block frequency band for which most fibers may be depleted, and a kHz conduction block frequency band for which most fibers have their action potentials blocked. By way of example, the nerve stimulation frequency band may extend up to about 50 Hz, the depletion block frequency band may extend between about 100 Hz to about 700 Hz, and the kHz conduction block frequency band may extend from about 5 kHz to 100 kHz. There may be transition frequencies between the bands, such as a transition between about 50 Hz to about 100 Hz or between about 70 Hz to 130 Hz for example and another transition between about 700 Hz to about 5 kHz. The response of the nerve to the stimulation frequency appears to depend on the transmitter and the synaptic end organ. Thus, different types of fibers may react differently for frequencies within the transition frequencies. By way of example, one frequency may cause an activation or neural stimulation of some fibers, and cause a depletion block in other fibers. The stimulation may be limited to specific fibers by the diameter or origin of the fibers or the location of the electrodes. For example, a frequency of the depletion block stimulation may be found to discriminate between afferent and efferent nerve fibers, or to discriminate between different fibers that emit different types of neurotransmitters. Such a frequency capable of providing both depletion block and activation/stimulation may be found in a transition region, but also may be found in one of the frequency bands such as within the depletion block frequency band.

Although the response to different frequencies may and is expected to change from application to application, the stimulation parameters for delivering a depletion block are expected to be available in current devices at reasonable energy consumption costs. In the study illustrated in the table where stimulation is provided at a pulse width of 300 µs, A-fibers were blocked at 2 mA, 200 Hz while still exciting B fibers that drove heart rate down at 5 mA, 20 Hz. A-fibers were responsible for the laryngeal motor fibers recorded via EMG. Small parasympathetic efferent B-fibers have a higher activation threshold are typically are responsible for heart rate control in the SA node. This example showed that NMJ block, just as activation via electrical stimulation, is graded to the size of the fiber axon being targeted As illustrated in Table 2, the speed of the depletion block depends on the frequency of the stimulation, where higher frequencies within the range of about 100 Hz to about 1 kHz provide the neurotransmitter block more quickly than the lower frequencies within that range. According to some embodiments, the depletion block may be implemented by a process that initiates the depletion block at a relatively high frequency (e.g. about 200 Hz to 400 Hz) to achieve fast depletion (e.g. about 50 ms or less), and then subsequently lower the frequency of the depletion block stimulation to about 100 Hz to maintain the block. As the lower frequency stimulation delivers fewer pulses, the lower frequency depletion block is more energy efficient than the higher frequency depletion block. If the depletion block was started at about 100 Hz rather than 200 Hz, it would take longer to achieve the depletion block. Based on current observations, it is believed that the depletion block at 100 Hz will take about 5 seconds to 10 seconds. The use of two (or more) stages of frequencies can be used to obtain benefits of each frequency, such as inducing depletion block relatively quickly using one frequency and then maintaining depletion block relatively efficiently using another frequency.

Various embodiments may use a depletion block at the synaptic junction to provide selective fiber communication. A depletion block may be limited to specific fibers by diameter or origin or location to the electrode. The amplitude of the depletion block pulses can be controlled to be greater than only the stimulation threshold for only some of the nerve fibers. Thus, although all fibers may be with other pulses that causes action potentials to propagate, the pre-synaptic terminal for some of the fibers are quickly depleted from their ability to communicate across the synaptic junction because the frequency of the stimulation causes the depletion block. Various stimulation waveforms may be used including non-sinusoidal or sinusoidal waveforms. Non-sinusoidal waveforms may include rectilinear pulses, charge balanced waveforms that may include biphasic rectangular pulses, quasi-trapezoidal for unidirectional applications, and pulsed triangular. Neural stimulation that elicits nerve traffic and a desired physiological response as part of neural stimulation therapy may be referred to as a low frequency stimulation (e.g. about 20 Hz or within a range of about 0.25 Hz to about 50 Hz); whereas in comparison a depletion frequency may be referred to as high frequency (e.g. about 200 Hz or within a range of about 100 Hz to about 1 kHz). The stimulation at these lower frequencies that is effective in activating nerve fiber(s) to deliver a nerve stimulation therapy may be referred to herein simply as "nerve stimulation" or "neural stimulation;" whereas the stimulation at the higher "depletion" frequencies may be referred to herein simply as a "depletion block stimulation." A "high amplitude, low frequency" (HALF) stimulation signal may exceed a stimulation threshold and thus may be used to recruit both small and big fibers. As such, a HALF signal may be used to obtain the desired effect of the stimulation by capturing all the necessary A sensory and B efferent fibers. A "small amplitude, high frequency" (SAHF) stimulation signal may be set at an amplitude that it only exceeds a smaller stimulation threshold and thus only recruits some of the fibers with the lower stimulation threshold (e.g. bigger fibers or fibers closer to the stimulation electrode(s)), while leaving other fibers with a higher stimulation threshold (e.g. smaller fibers or fibers further away from the stimulation electrode(s)) still excitable with the HALF stimulation. The depletion block stimulation cancels the effectiveness of all signals that are evoked at lower frequencies (e.g. 20 Hz) with the same or lower amplitude. SAHF may be used to achieve the neurotransmitter depletion block of the large fibers which are the fibers with relatively low stimulation thresholds but not the smaller fibers which are the fibers with relatively high stimulation thresholds. In some embodiments, the higher frequency depletion block stimulation may be delivered using the same or approximately the same high amplitude as the low frequency stimulation to reduce or modulate the effect of the applied therapy using the low frequency stimulation.

The current amplitude and the pulse width control whether an axon is depolarized, and the frequency of the stimulation controls whether the neurotransmitters are depleted at the nerve ending. The current amplitude and pulse width may be controlled to select only larger fibers for the depletion block. For example, the current amplitude and pulse width may be controlled to deplete the A fibers and not the smaller fibers, or may be controlled with higher amplitudes and/or wider pulse widths to deplete both A and B fibers.

By way of example and not limitation, a full neurotransmitter block for intended fibers may be ensured by acquiring a recruitment curve. The recruitment curve may identify the activation threshold and saturation threshold for the neural target. The recruitment curve may be specific to an individual patient, may illustrate an increase in activity with increasing current amplitude, and may then illustrate a plateau where the activity does not significantly increase with increasing current amplitude. The activation threshold reflects where the nerve activity begins to increase with increasing current amplitude, and the saturation threshold reflects where the nerve activity does not significantly increase in response to further increases in current amplitude. The current amplitude for the depletion block stimulation may be determined based on the activation threshold, as it may be set at a margin higher than the activation threshold. The saturation threshold indicates a threshold where all or almost all of the nerve fibers propagate action potentials. The current amplitude for the depletion block stimulation may be higher than and based on the saturation threshold of the fibers that are intended to be blocked. By way of example, the amplitude of the depletion stimulation signal may be set at approximately the saturation threshold of the fibers that are intended to be blocked, or may be set at a margin higher than the saturation threshold of the fibers, or may be set at a margin lower than the saturation threshold to provide a partial block.

A procedure can be implemented to determine each individual patient's selective fiber stimulation therapy profile, as there may be patient variation or variations resulting from electrode spacing from nerves fibers. The particular procedure will depend on the particular neural target that is stimulated, as the nerve fibers in different neural targets innervate different portions of the body. For example, if a cervical vagus nerve is targeted, the patient's selective fiber stimulation therapy profile may be determined by observing laryngeal vibration as well as blood pressure and heart rate fluctuations. Thus, various embodiments for providing a depletion block may first find an activation threshold and saturation threshold for a neural target. The current amplitude may be selected to be above the saturation threshold of the neural target, and the frequency may be selected for a given application to be high enough (e.g. 200 Hz) to quickly deplete the presynaptic terminal of its ability to communicate across the synaptic cleft to provide an effective depletion block for that application. The procedure may transition the frequency of the stimulation while monitoring the physiological effects to transition between different types of block (e.g. transition between depletion block and kHz conduction block), or to improve efficiency, or to improve time constants (e.g. onset/restoration), or to find a desired frequency and location that both activates some nerve fibers and also provides a depletion block for other nerve fibers.

Some embodiments may ramp up stimulation. Ramping up the stimulation may provide a graded block that may make the stimulation more tolerable. In a neural muscular junction depletion block, for example, the ramped stimulation may reduce the force of the one initial muscle activity at start of stimulation by creating an initial period of graded block. Some embodiments may change the frequency of stimulation signal during the block. Thus, higher frequency stimulations may be used to quickly obtain the block, and then lower frequency stimulation may be used to maintain the block that was previously obtained. For example, an initial frequency (e.g. 260 Hz) may be used to quickly achieve depletion block followed by a second frequency (e.g. 130 Hz) to maintain the depletion block. The frequency of stimulation is related to how long for complete or 90% depletion block. For example, frequencies within the range of about 100 to about 150 Hz provide a 90% depletion block in about 10 to 4 seconds, and frequencies within the range of about 200 to 1000 Hz provides a 90% depletion block less than one second (e.g. on the order of milliseconds). Frequencies greater than 1 kHz start to enter into nerve conduction block.

Figure 6:
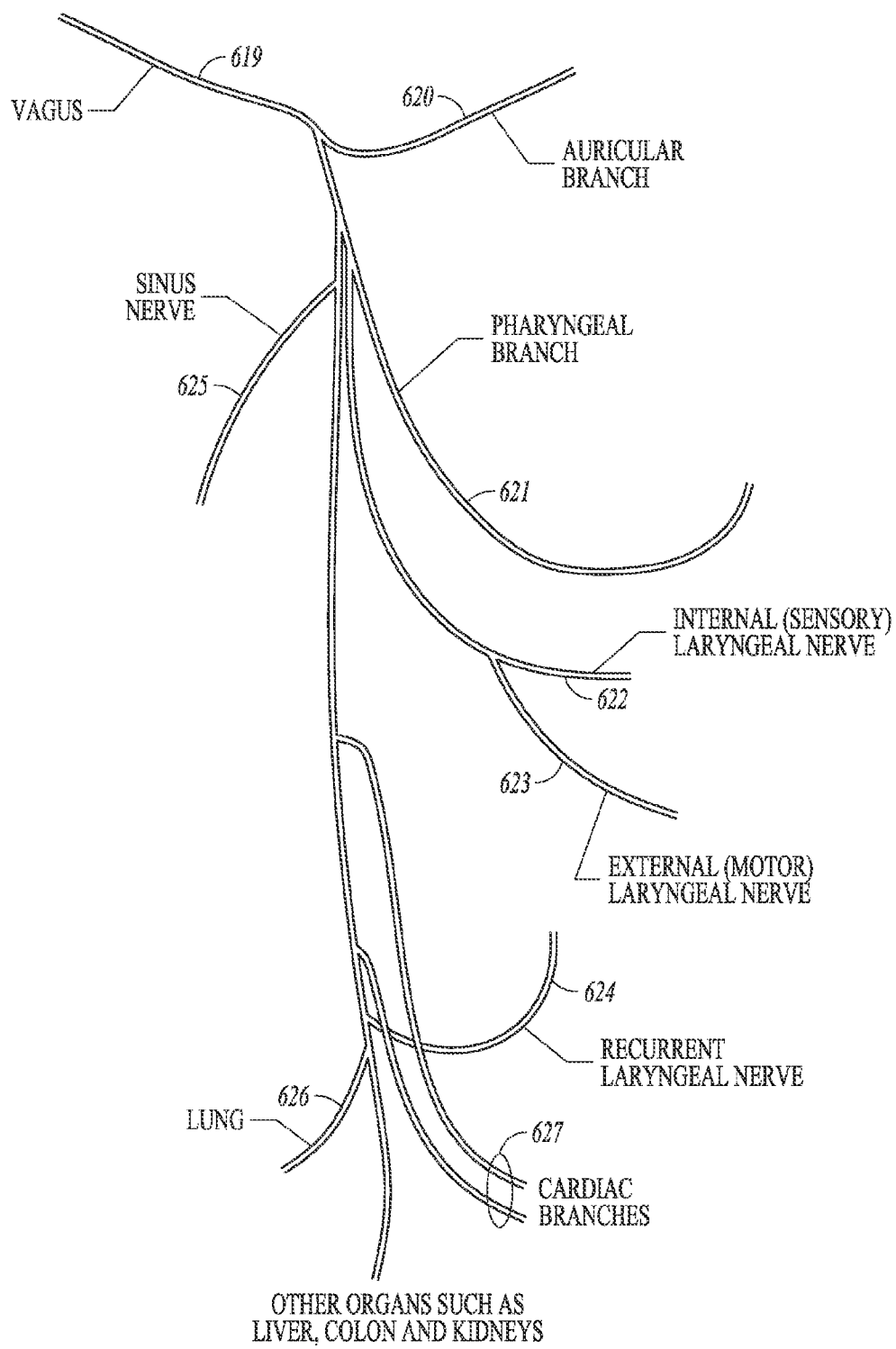
FIG. 6 illustrates some branches from the cervical vagus nerve.

The present subject matter may be used in applications that stimulate the vagus nerve, or in applications that stimulate other nerves. The vagus nerve is discussed herein as an example of a complex nerve. The vagus nerve is part of the autonomic nervous system (ANS) which is briefly discussed below. FIG. 6 illustrates some branches from the cervical vagus nerve. The cervical vagus nerve 619 is a combined nerve that separates into a number of branches, including the auricular branch 620 which innervates areas around the ear, the pharyngeal branch 621 that innervates areas around the pharynx, the internal 622 laryngeal nerve, external laryngeal nerve 623 and recurrent laryngeal nerve 624 that innervate areas around the larynx, the sinus nerve branch 625 which innervates the carotid sinus along with branches from the glossopharyngeal nerve, pulmonary branches 626 that innervate the lungs, and cardiac branches 627 that innervate the heart. The vagus nerve continues to innervate other portions of the body including the liver, stomach, intestines, bladder and kidneys. The fibers that innervate the heart for example include smaller B-fibers. Therapies, such as a heart failure therapy, that stimulate the cervical vagus nerve have been proposed. It may desirable to stimulate the cervical vagus nerve in a manner that activates the smaller diameter B-fibers (parasympathetic) without activating larger diameter A-fibers (motor) so as to avoid unwanted side effects that may occur from activating the A-fibers such as but not limited to laryngeal vibration, cough and various unpleasant feelings.

The ANS regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example. The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent nerves convey impulses toward a nerve center, and efferent nerves convey impulses away from a nerve center.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases may be referred to herein as neurocardiac therapy (NCT). Vagal stimulation used to treat cardiovascular diseases may be termed either VST or NCT. However, VST may be delivered for non-cardiovascular diseases, and NCT may be delivered by stimulating a nerve other than the vagal nerve. Examples of cardiovascular diseases or conditions include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

The vagus has many neural pathways that are recruited at different stimulation thresholds. Various physiological responses to vagal stimulation are associated with various thresholds of VST intensity. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal, a stimulation burst frequency, a pulse width and/or a duty cycle.

Figure 7:
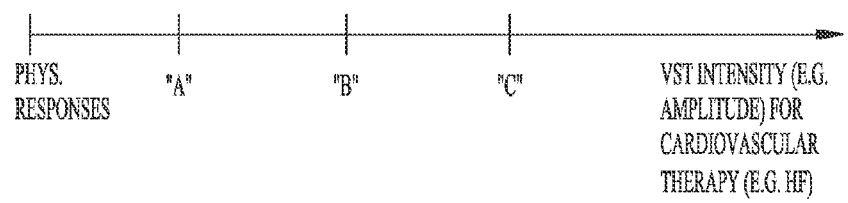
FIG. 7 illustrates increasing VST intensity from the left side to the right side of the figure, and further illustrates intensity thresholds that elicit various physiological responses to VST.

For example, FIG. 7 illustrates increasing VST intensity from the left side to the right side of the figure, and further illustrates intensity thresholds that elicit various physiological responses to VST. VST causes a physiological response "A" at a lower intensity than an intensity at which VST causes a physiological response "B", which occurs at a lower VST intensity than an intensity at which VST causes a physiological response "C". Stated another way, VST triggers response "A" after reaching a certain level of intensity (e.g. a stimulation threshold), triggers response "B" along with response "A" after reaching a higher intensity (e.g. a higher stimulation threshold), and triggers response "C" along with responses "A" and "B" after reaching an even higher intensity (e.g. an event higher stimulation threshold).

As identified above VST may be used to treat cardiovascular diseases. The beneficial effects of VST on cardiac function and remodeling are not necessarily mediated via heart rate reduction. That is, VST can benefit patients without undesired chronotropic effects associated with VST as well as other side effects due to high intensity stimulation such as coughing, muscle stimulation, etc. Rather, anti-inflammatory, anti-sympathetic, and anti-apoptosis mediators are triggered at lower VST intensities than intensities at which a heart rate reduction is realized. These mediators function as pathways through which the VST provides the therapeutic effects for cardiovascular disease. Physiological responses at the lower VST intensities have therapeutically-effective results for cardiovascular diseases such as HF. These responses mediate or provide pathways for these therapies. Examples of such responses that are beneficial for HF at the lower VST intensities include anti-inflammation, anti-sympathetic, and anti-apoptosis responses, and an increased nitric oxide (NO). Physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing. Further, some physiological responses at lower VST intensities also may not be desirable. For example, patients may find laryngeal vibrations to be unpleasant. At least some of these responses may be desirable for some therapies but not desirable for other therapies. By way of example and not limitation, VST that reduces heart rate and or that prolongs AV conduction may be desirable to treat some cardiovascular conditions, but may not be desirable for others. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal (e.g. a frequency of stimulation pulses), a stimulation burst frequency (e.g. a plurality of bursts delivered at a burst frequency for initiating bursts where each burst includes a plurality of pulses), a pulse width and/or a duty cycle.

The present subject matter may be used to set or limit the intensity of the threshold to avoid undesired effects of high intensity stimulation, and may also be used to provide a depletion block for some undesired effects at the lower stimulation intensities. For example, a depletion block may be implemented to block response "A" and the intensity of the stimulation may be set to avoid response "C", thus leaving the desired response "B" to the stimulation. Some embodiments provided herein may deliver a presynaptic terminal block to block undesired activations at lower thresholds such as can cause laryngeal vibrations, while delivering the VST intensity above the lower boundary. By blocking the undesired activations at lower thresholds, it may be possible to increase the intensity of the stimulation to capture more of the desired fibers and improve the desired response to the stimulation.

Figure 8:
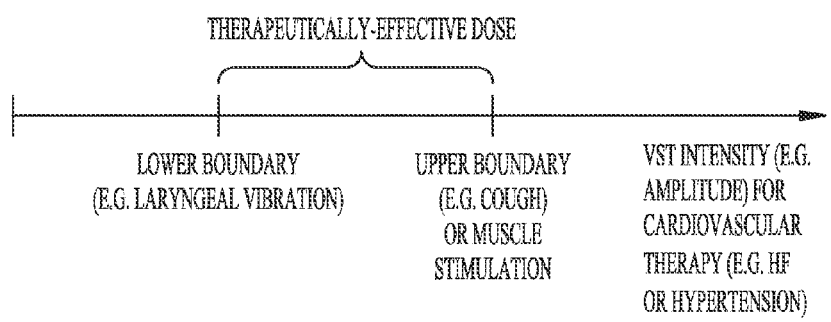
FIG. 8 illustrates increasing VST intensity from the left side to the right side of the figure, and further illustrates an intensity threshold that elicits an undesired physiological response to VST that is used to define an upper boundary for the VST intensity and another intensity threshold that elicits another physiological response to VST.

FIG. 8 illustrates increasing VST intensity from the left side to the right side of the figure, and further illustrates an intensity threshold that elicits an undesired physiological response to VST that is used to define an upper boundary for the VST intensity and another intensity threshold that elicits another physiological response to VST. For example, the VST intensity threshold for a cough can be used as an upper boundary, and the VST intensity threshold for a laryngeal vibration response can be used as a lower boundary. In some embodiments, the physiological response to define the upper boundary is detected muscle stimulation. Large muscle stimulation or extraneous stimulation may be bothersome to the patient. A vagus nerve capture threshold can be set by first recruiting A fibers that cause laryngeal vibrations, and then increasing the intensity until a cough side effect is detected. The intensity is set between the intensity that caused the laryngeal vibrations and the intensity that caused the cough. For example, if the amplitude of the stimulation signal is increased to increase the VST intensity and if 1.0 mA caused laryngeal vibrations and 2.5 mA caused a cough, then the pacing amplitude may be set to 1.0 to 2.4 mA. The depletion block may be applied with appropriate stimulation parameters to block the VST from causing laryngeal vibrations or other undesired responses induced at lower amplitudes.

Figure 9A:
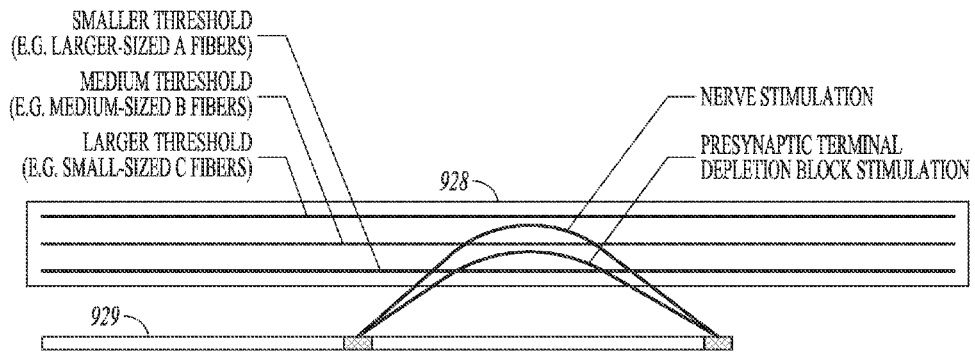
FIGS. 9A-9C illustrate selective stimulation using a simple illustration of different stimulation thresholds for different fiber types in a complex nerve 928, and further using different combinations of nerve stimulation and presynaptic terminal depletion block stimulation.
Figure 9B:
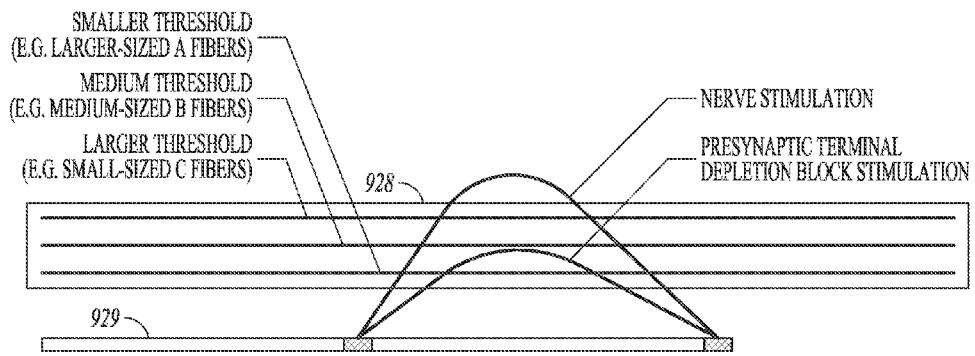
Figure 9C:
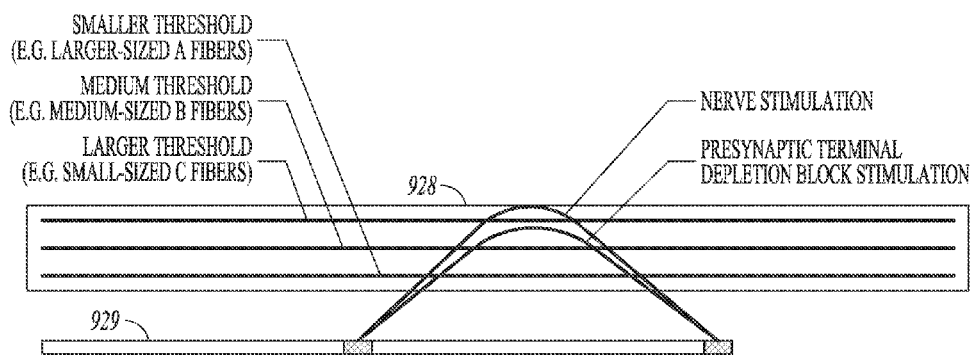

FIGS. 9A-9C illustrate selective stimulation using a simple illustration of different stimulation thresholds for different fiber types in a complex nerve 928, and further using different combinations of nerve stimulation and presynaptic terminal depletion block stimulation. By way of example and not limitation, each of FIGS. 9A-9C include bipolar stimulation lead 929 configured to deliver both nerve stimulation and presynaptic terminal depletion block stimulation. The concept illustrated in these figures may apply to other types of stimulation such unipolar stimulation and multipolar stimulation. The figures provide a simple illustration of a nerve showing, by way of a simple example, three stimulation thresholds identified as a smaller threshold, a medium threshold and a larger threshold. The threshold for a given fiber is dependent on it fiber type as well as its location to the stimulation electrodes. However the concept may be simply illustrated based on fiber size. The simple illustration in FIGS. 9A-9C have larger-sized A type fibers with a smaller stimulation threshold, a medium-sized B type fibers with a medium stimulation threshold, and a smaller-sized C type fibers with a larger stimulation threshold. FIG. 9A illustrates selective stimulation of the medium-sized B type fibers with a medium stimulation threshold. The nerve stimulation has parameters to exceed the stimulation threshold of both the A and B fibers, and the depletion block has parameters to exceed the stimulation threshold of the A fibers. Thus, the combination of the nerve stimulation and the depletion block results in effectively stimulating only the B fibers as only the B fibers can communicate across their respective synaptic gap. FIG. 9B illustrates selective stimulation of the medium-sized B type fibers with a medium stimulation threshold and the smaller-sized C fibers with the smaller threshold. The nerve stimulation has parameters to exceed the stimulation threshold of the A, B and C fibers, and the depletion block has parameters to exceed the stimulation threshold of the A fibers. Thus, the combination of the nerve stimulation and the depletion block results in effectively stimulating only the B and C fibers as only the B and C fibers can communicate across their respective synaptic gap. FIG. 9C illustrates selective stimulation of the smaller-sized C fibers with the smaller threshold. The nerve stimulation has parameters to exceed the stimulation threshold of the A, B and C fibers, and the depletion block has parameters to exceed the stimulation threshold of the A and B fibers. Thus, the combination of the nerve stimulation and the depletion block results in effectively stimulating only the C fibers as only the C fibers can communicate across their respective synaptic gap.

Figure 10:
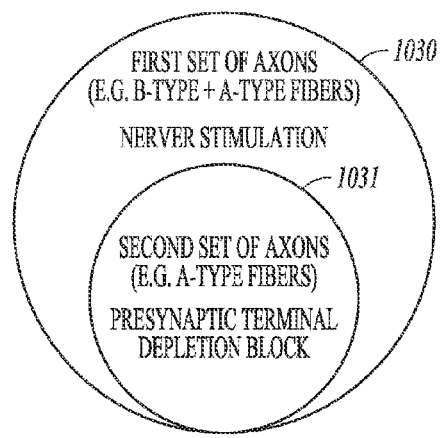
FIG. 10 illustrates a first set of axons 1030 in a nerve captured by nerve stimulation and a second set of axons 1031 captured by depletion block stimulation, wherein the second set of axons is a subset of the first set of axons.

FIG. 10 illustrates a first set of axons 1030 in a nerve captured by nerve stimulation and a second set of axons 1031 captured by depletion block stimulation, wherein the second set of axons is a subset of the first set of axons. The nerve stimulation is larger than a threshold for stimulation the first set of axons, and thus will cause action potentials to propagate in the larger, first set of axons. However, the depletion block will prevent the presynaptic terminals of the subset of axons from conducting across their respective synaptic cleft, and only the remainder of the first set of axons is effective in communicating across the synaptic cleft.

FIGS. 11A-11M illustrate some examples of electrode configurations that may be used to deliver the selective neural stimulation using depletion block stimulation. These examples are not intended to show all possible electrode configurations. The electrode configurations may be bipolar configurations or unipolar configurations. Further, the spacing between electrodes may vary from that which is illustrated. Also, these examples are not intended to necessarily represent timing between the nerve stimulation and the depletion block stimulation. Some embodiments may interrupt the depletion block stimulation (e.g. 200 Hz) to provide windows of time within which a pulse of the nerve stimulation (e.g. 20 Hz) is delivered, thus avoiding simultaneous delivery of two signals using more than one cathode and/or more than one anode. The polarity of the signals may be switched. Some embodiments may share a cathode for both the nerve stimulation and the depletion block stimulation, and some embodiments may share an anode for both the nerve stimulation and the depletion block stimulation.

Figure 11A:
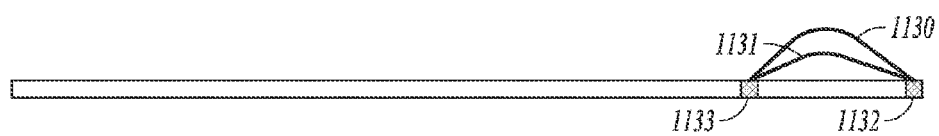
FIGS. 11A-11M illustrate some examples of electrode configurations that may be used to deliver the selective neural stimulation using depletion block stimulation.
Figure 11B:
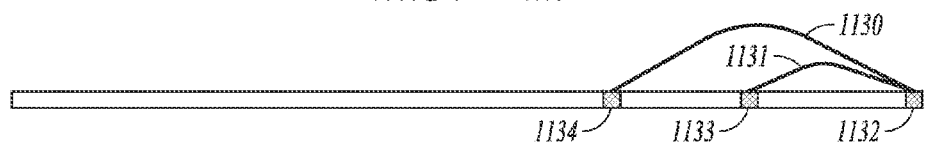
Figure 11C:
Figure 11D:
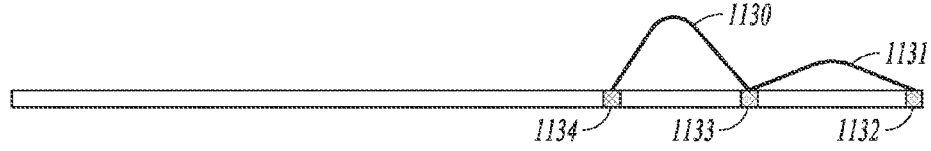
Figure 11E:
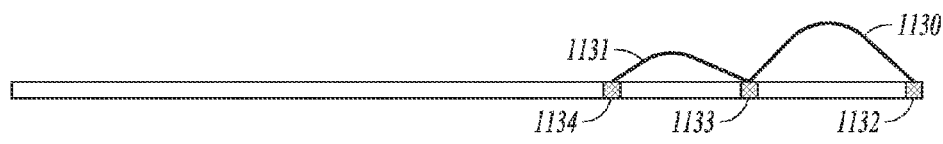
Figure 11F:
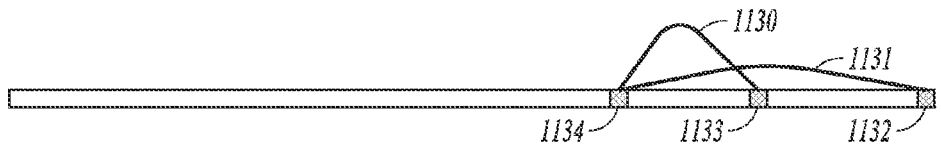
Figure 11G:
Figure 11H:
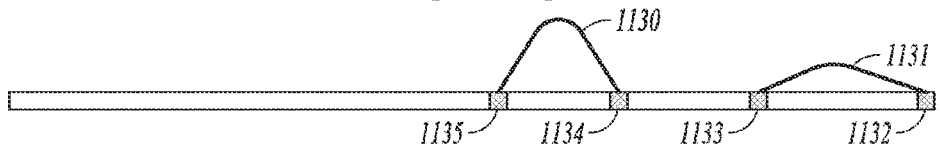
Figure 11I:
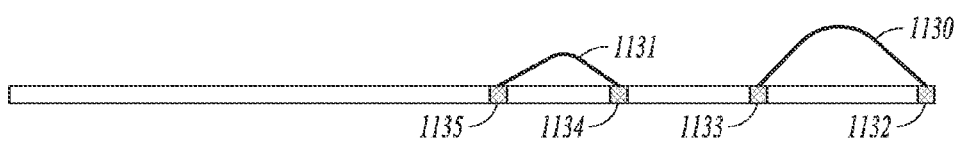
Figure 11J:
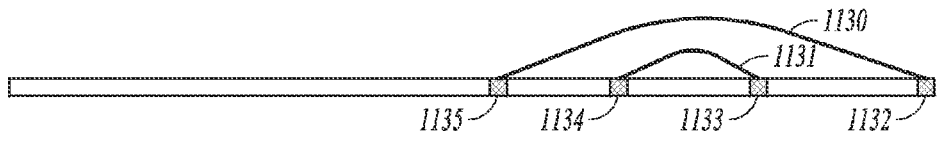
Figure 11K:
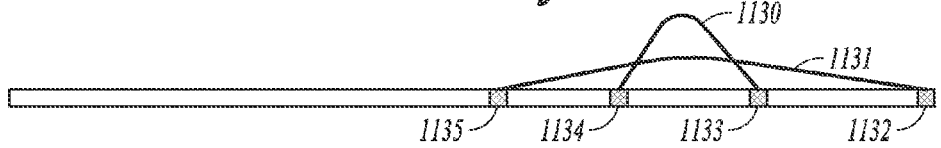
Figure 11L:
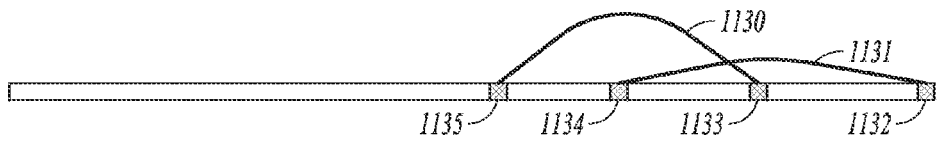
Figure 11M:
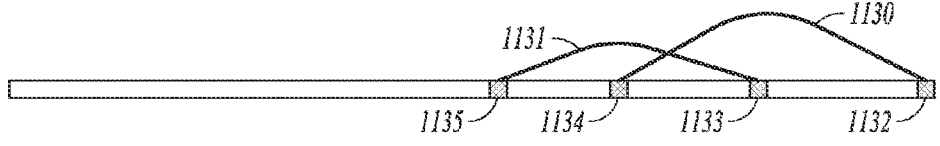

FIG. 11A illustrates an electrode configuration in which a first electrode 1132 and a second electrode 1133 are used to deliver the nerve stimulation 1130, and are used to also deliver the depletion block 1131. There may be some anatomical locations which are more amenable to stimulation using some other electrode arrangements than others. Some of these are illustrated below. Some embodiments may be configured to electronically switch the stimulation vectors among available electrodes on the lead. FIG. 11B illustrates an electrode configuration including a first electrode 1132, a second electrode 1133 and a third electrode 1134 in which a first electrode 1132 and a third electrode 1134 are used to deliver the depletion block 1131 and first electrode 1132 and a third electrode 1134 are used to deliver the nerve stimulation 1130. FIG. 11C illustrates an electrode configuration including a first electrode 1132, a second electrode 1133 and a third electrode 1134 in which the first electrode 1132 and the third electrode 1134 are used to deliver the nerve stimulation 1130, and the second electrode 1132 and the third electrode 1134 are used to also deliver the depletion block 1131. FIG. 11D illustrates an electrode configuration including a first electrode 1132, a second electrode 1133 and a third electrode 1134 in which the first electrode 1132 and the second electrode 1133 are used to deliver the depletion block 1131, and the second electrode 1133 and the third electrode 1134 are used to deliver the nerve stimulation 1130. FIG. 11E illustrates an electrode configuration including a first electrode 1132, a second electrode 1133 and a third electrode 1134 in which the second electrode 1133 and the third electrode 1134 are used to deliver the nerve stimulation 1130, and the first electrode 1132 and the third electrode 1134 are used to deliver the depletion block 1131. FIG. 1 IF illustrates an electrode configuration including a first electrode 1132, a second electrode 1133 and a third electrode 1134 in which the first electrode 1132 and the third electrode 1134 are used to provide the depletion block 1131 and the second electrode 1133 and the third electrode 1134 are used to provide the nerve stimulation 1130. FIG. 11G illustrates an electrode configuration including a first electrode 1132, a second electrode 1133 and a third electrode 1134 in which the first electrode 1132 and the second electrode 1133 are used to deliver the nerve stimulation 1130, and the first electrode 1132 and the third electrode 1134 are used to deliver the depletion block 1131. FIG. 11H illustrates an electrode configuration including a first electrode 1132, a second electrode 1133, a third electrode 1134, and a fourth electrode 1135 in which the first electrode 1132 and the second electrode 1133 are used to deliver the depletion block 1131 and the third electrode 1134 and the fourth electrode 1135 are used to deliver the nerve stimulation 1130. FIG. 11I illustrates an electrode configuration including a first electrode 1132, a second electrode 1133, a third electrode 1134, and a fourth electrode 1135 in which the first electrode 1132 and the second electrode 1133 are used to deliver the nerve stimulation 1130 and the third electrode 1134 and the fourth electrode 1135 are used to deliver the depletion block 1131. FIG. 11J illustrates an electrode configuration including a first electrode 1132, a second electrode 1133, a third electrode 1134, and a fourth electrode 1135 in which the first electrode 1132 and the fourth electrode 1135 are used to deliver the nerve stimulation 1130 and the second electrode 1133 and the third electrode 1134 are used to deliver the depletion block 1131. FIG. 11K illustrates an electrode configuration including a first electrode 1132, a second electrode 1133, a third electrode 1134, and a fourth electrode 1135 in which the first electrode 1132 and the fourth electrode 1135 are used to deliver the depletion block 1131 and the second electrode 1133 and the third electrode 1134 are used to deliver the nerve stimulation 1130. FIG. 11L illustrates an electrode configuration including a first electrode 1132, a second electrode 1133, a third electrode 1134, and a fourth electrode 1135 in which the first electrode 1132 and the third electrode 1134 are used to deliver the depletion block 1131 and the second electrode 1133 and the fourth electrode 1135 are used to deliver the nerve stimulation 1130. FIG. 11M illustrates an electrode configuration including a first electrode 1132, a second electrode 1133, a third electrode 1134, and a fourth electrode 1135 in which the first electrode 1132 and the third electrode 1134 are used to deliver the nerve stimulation 1130 and the second electrode 1133 and the fourth electrode 1135 are used to deliver the depletion block 1131.

Figure 12:
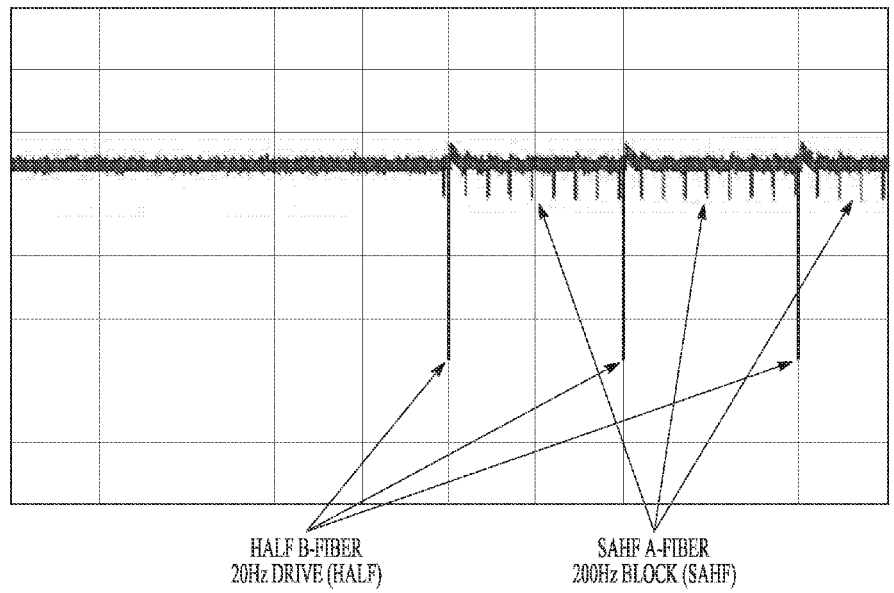
FIG. 12 illustrates, by way of example and not limitation, concurrent delivery of both nerve stimulation and depletion block stimulation.

FIG. 12 illustrates, by way of example and not limitation, concurrent delivery of both nerve stimulation and depletion block stimulation. For example, various embodiments may provide a stimulator capable of delivering a blocking waveform for blocking the A fibers simultaneously with a therapy waveform for eliciting action potentials in the B fibers. In a more specific example, A fibers may be blocked using a 200 Hz frequency at a low current amplitude sufficient to reach the stimulation threshold for the A fibers but not sufficient to reach the stimulation threshold for B fibers. Such a stimulation signal may effectively block A fibers but not block the B fibers. The therapy to drive action potentials in the B-fiber may be delivered at 20 Hz and at a high current amplitude sufficient to reach the stimulation threshold for both A fibers and B fibers. As the A fibers are blocked by the presynaptic terminal depletion block at 200 Hz frequency at a low current amplitude, action potentials will not be driven by the 20 Hz signal. The combined waveform may be on one bipolar electrode. In comparison to each other, the 20 Hz signal has a relatively high amplitude and a relatively low frequency and thus may be referred to as a high amplitude low frequency (HALF) signal; and the 200 Hz signal has a relatively small amplitude and a relatively high frequency and thus may be referred to as a small amplitude high frequency (SAHF) signal. Activation of therapeutic B-fibers leads to a reduction in HR, whereas locking unwanted A-fibers stops laryngeal vibration.

Figure 13:
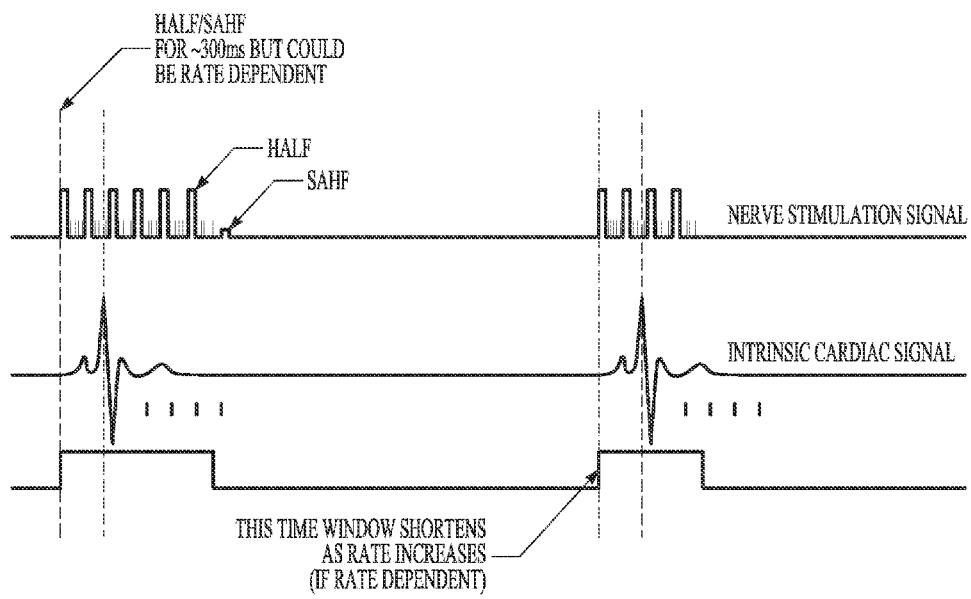
FIG. 13 illustrates, by way of example and not limitation, intermittent delivery of concurrent nerve stimulation and depletion block stimulation.

FIG. 13 illustrates, by way of example and not limitation, intermittent delivery of concurrent nerve stimulation and depletion block stimulation. The intermittent delivery includes stimulation ON times separated by stimulation OFF times. The stimulation ON times may be scheduled to occur at programmed times, such as a programmed start time and programmed stop time or a programmed start time and a programmed duration. An example of intermittent delivery includes ten seconds ON/50 seconds OFF. By way of example, stimulation ON periods maybe for a time period within a range between a ¼ of a second and 150 seconds, and the stimulation OFF periods are for a time period between 1 second and 150 seconds. The onset for the depletion block is quick enough to allow for short period bursting. The stimulation ON times may be triggered by detected events. The detected events may be receipt of a patient command or a clinician command. The detected events may be a detected event determined from sensed parameter(s). For example, as illustrated by an example of an intrinsic cardiac signal in FIG. 13, the stimulation may be triggered when a specific portion of a cardiac cycle is detected using a sensed parameter such as heart rate, or ECG, heart sounds, or blood pressure. The duration of the stimulation delivered in response to the detected event may be a programmed fixed event or may be variable based on the detected event or the frequency of the detected events. For example, a window of time for delivering the stimulation may be shortened in response to an increased rate of stimulation.

Figure 14:
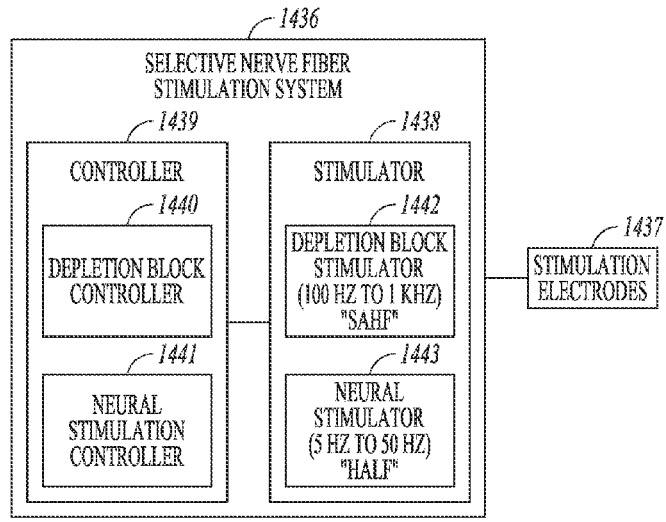
FIG. 14 illustrates by way of example and not limitation an example of a selective nerve fiber stimulation system.

FIG. 14 illustrates by way of example and not limitation an example of a selective nerve fiber stimulation system. The system 1436 may be connected to stimulation electrodes 1437. The system 1436 may include a stimulator 1438 and a controller 1439 operably connected to the stimulator 1438 to control the delivered stimulation. The controller 1439 may include a depletion block controller 1440 and a neural stimulation controller 1441, and the stimulator 1438 may include a depletion block stimulator 1442 and a neural stimulator 1443. The depletion block controller 1440 may be operably connected to the depletion block stimulator 1442 to control delivery of the depletion block stimulation, which has a frequency within a range of about 100 Hz to about 1 kHz. This depletion block stimulation may be referred to as SAHF for some selective nerve fiber stimulation embodiments. The neural stimulation controller 1441 may be operably connected to the neural stimulator 1443 to control delivery of the nerve stimulation, which may a frequency within a range of about 0.25 Hz to about 50 Hz. For example, the frequency of the nerve stimulation signal may be about 20 Hz. This nerve stimulation signal may be referred to as a HALF signal.

Figure 15:
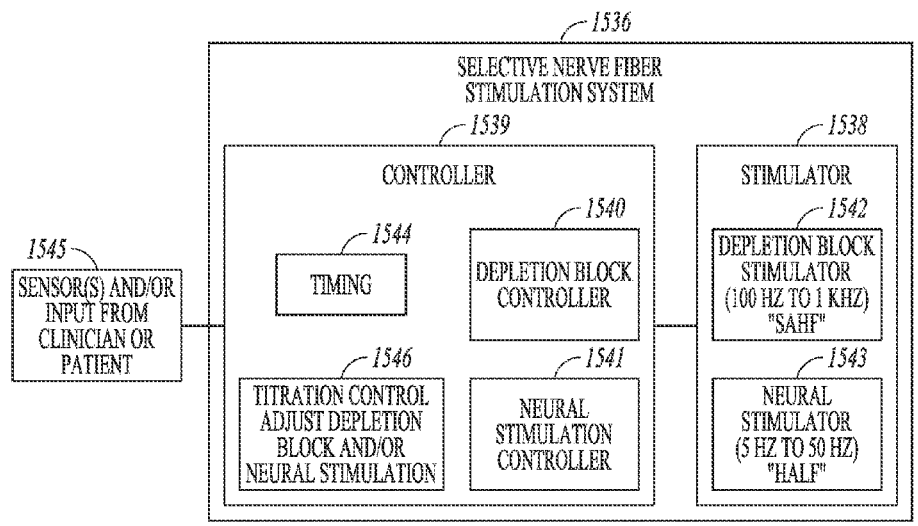
FIG. 15 illustrates by way of example and not limitation an example of a selective nerve fiber stimulation system.

FIG. 15 illustrates by way of example and not limitation an example of a selective nerve fiber stimulation system. The system 1536 has similarities to FIG. 14, including a controller 1539 that includes a depletion block controller 1540 and a neural stimulation controller 1541, and further including a stimulator 1538 that includes a depletion block stimulator 1542 and a neural stimulator 1543 similar to those shown and described in FIG. 14. The controller 1539 may further include a timing module 1544 configured to control timing of the stimulation. The timing may be controlled in a variety of ways. The timing module may be configured to control the timing of both the depletion block and the neural stimulation. For example, the timing module may control the start and stop times for both the depletion block and the neural stimulation. The timing module may control the start and duration times for both the depletion block and neural stimulation. The timing module may control the timing of changes to the depletion block stimulation or changes to the neural stimulation. For example, the timing module may control the change from a first depletion block stimulation frequency to a second depletion block stimulation frequency. The timing module may control the relative timing between the depletion block and the neural stimulation. For example, the depletion block stimulation may depend on the timing of the neural stimulation. Further, the depletion block stimulation may be interrupted to provide a window in which a pulse of the nerve stimulation is delivered. The depletion block may be initiated simultaneously with the nerve stimulation, or may be initiated slightly before or slightly after the initiation of the nerve stimulation. For example, according to Table 2, a 200 Hz signal depletion block signal may begin less than one second before the nerve stimulation so that more than 90% block is achieved before the nerve stimulation begins. As generally illustrated at 1545 the timing may be based on commands or other input from a clinician or patient, or may be based on physiologic sensors such as, by way of example and not limitation, respiration sensors, blood pressure sensors, blood flow sensors, or cardiac sensors which may include information about the cardiac cycle and heart rate information.

The controller 1539 may further include a titration control module 1546. The titration control module may be used to adjust the depletion block stimulation to control the axons that are captured by the depletion block stimulation, to adjust the nerve stimulation to control the axons that a captured by the nerve stimulation, or to adjust both the depletion block stimulation and the nerve stimulation. The amplitude of the stimulation may be adjusted, or the pulse width may be adjusted, or both the amplitude and pulse width may be adjusted to control the axons that are captured.

Titration, as used herein, refers to the process of adjusting the dose of the stimulation which may be a depletion block stimulation, a nerve stimulation or both a depletion block and nerve stimulation, ultimately to a level that is therapeutically or prophylactically effective. An effective depletion block stimulation may be stimulation at a depletion block frequency (e.g. 100 Hz to 1 kHz) with an amplitude and pulse width effective to capture the desired axons. An effective nerve stimulation may be stimulation at a nerve stimulation frequency (e.g. 0.25 Hz to 50 Hz, such as about 20 Hz) with an amplitude and pulse width effective to capture the desired axons. Furthermore, the nerve stimulation also has a "dose" component to provide an effective amount of stimulation to provide the desired therapy. The dose includes an amount or intensity of the neural stimulation at a given time frame, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time. The titration procedure may occur during an implantation procedure, or during a follow-up clinical visit, or while a patient is ambulatory away from the clinical setting. The titration may be physician-controlled or automatically-controlled based on device programming. As generally illustrated at 1545, the titration may be based on commands or other input from a clinician or patient, or may be based on physiologic sensors such as, by way of example and not limitation, respiration sensors such as minute ventilation sensors, blood pressure sensors, blood flow sensors, impedance sensors, an accelerometer, an electromyogram (EMG) sensor, or cardiac sensors which may include information about the cardiac cycle and heart rate information such as a sensor configured to detect an electrocardiogram (EKG). Cardiac sensors may include electrodes and heart sound sensors, for example.

As illustrated in FIG. 13, the neural stimulation and/or depletion block may be intermittent. FIG. 16 illustrates, by way of example, a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 1647) is delivered, and intervals of stimulation being OFF, when no stimulation pulses are delivered. Thus, for example, some embodiments deliver a plurality of monophasic or biphasic pulses within a neural stimulation burst illustrated in FIG. 16. Pulses delivered within a burst 1647 may be delivered at a pulse frequency. These pulses also have an amplitude. Both the pulse frequency and the pulse amplitude affect the dose of the neural stimulation therapy. The duration of the stimulation ON interval is sometimes referred to as the stimulation duration or burst duration. The burst duration also affects the dose of the neural stimulation therapy. The start of a stimulation ON interval is a temporal reference point NS Event. The time interval between successive NS Events is the INS Interval, which is sometimes referred to as the stimulation period or burst period 1648. The burst period 1648 or the number of neural stimulation events that occur over a time period also affect the dose of the neural stimulation. For an application of neural stimulation to be intermittent, the stimulation duration (i.e., ON interval) is less than the stimulation period (i.e., INS Interval) when the neural stimulation is being applied. The duration of the OFF intervals of INS are determined by the durations of the ON interval and the INS Interval. The duration of the ON interval relative to the INS Interval (e.g., expressed as a ratio) is sometimes referred to as the duty cycle of the INS.

A physician or clinician may control the adjustment of one or more neural stimulation parameters to control the stimulation intensity. For example, during an implantation procedure in which stimulation electrodes are implanted near a vagus nerve or other neural stimulation target, the physician or clinician may adjust stimulation parameter(s) to adjust the stimulation intensity to appropriately position the electrodes and program the stimulation to provide threshold stimulation of the neural target that provides a desired physiological effect. The physician or clinician may re-program an implantable neural stimulator during a follow-up visit, to account for migration of the electrodes, changes in impedance in the electrode/tissue interface, and the like. During the follow-up visit, the physician or clinician may control the adjustment of one or more neural stimulation parameters to control the stimulation intensity to determine a neural stimulation intensity that provides the desired physiological response. The titration routine can be an automatic process for an implantable neural stimulation device implanted in an ambulatory patient. The automatic titration routine can be manually triggered by a signal from a patient or by the physician or clinician. The automatic titration routine can be automatically triggered by a programming schedule or by a sensed event.

FIG. 17 illustrates a memory 1749 which may be incorporated in the controller 1439 in FIG. 14 or 1539 in FIG. 15, according to various embodiments. The memory 1749 may include instructions 1780, operable on by the stimulation control circuitry, for controlling an up-titration routine by progressively stepping up through defined parameter sets (e.g. parameter set 1 through parameter set N), where each set incrementally changes (increases or decreases) the stimulation dose or intensity of the stimulation therapy. The memory may include a plurality of neural stimulation parameter sets, where each set includes a unique combination of parameter values for the neural stimulation and wherein each unique combination of parameter values is defined to provide neural stimulation therapy at an intensity level. The instructions include instructions for stepping through the plurality of neural stimulation parameter sets according to a schedule to change (increase or decrease) the intensity of the therapy until the therapy is at the desired long term intensity. Various embodiments provide a neural stimulation routine that automatically finds the desirable combination of therapy parameters (e.g. amplitude, pulse width, duty cycle) that provides a desired therapy intensity level.

FIG. 18 illustrates an embodiment of a therapy titration module 1851, which may be part of the titration control module 1546 in FIG. 15. According to various embodiments, the controller is adapted to set or adjust any one or any combination of stimulation features 1852. Examples of stimulation features include the amplitude, frequency, polarity and wave morphology of the stimulation signal. Some embodiments of the stimulation output circuit are adapted to generate a stimulation signal with a predetermined amplitude, morphology, pulse width and polarity, and are further adapted to respond to a control signal to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 1851 can be programmed to change an electrode set or electrode configuration or to change stimulation sites 11853, such as changing the stimulation electrodes used for a neural target or changing the neural targets for the neural stimulation. For example, different electrodes can be used to stimulate a neural target, and different electrodes can be used to stimulate different neural targets. A desirably low stimulation threshold for a neural target may be determined using different electrode sets/configurations for stimulating that neural target. Different neural targets can include different neural pathways such as the right and left vagus nerves and branches thereof, baroreceptor regions, chemoreceptor regions, the carotid sinus, and the carotid sinus nerve. Different neural targets may include different positions along a neural pathway (e.g. more caudal or more cranial targets along a cervical vagus nerve). Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 1851 can be programmed to change stimulation vectors 1854. Vectors can include stimulation vectors between electrodes, or stimulation vectors for transducers. For example, the stimulation vector between two electrodes can be reversed. More complicated combinations of electrodes can be used to provide more potential stimulation vectors between or among electrodes.

The therapy titration module 1851 can be programmed to control the neural stimulation according to stimulation instructions, such as a stimulation routine or schedule 1855, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation. A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session. According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, a particular position/posture, low heart rate levels, and the like. For example, the stimulation can be synchronized to the cardiac cycle based on detected events that enable the stimulation. The therapy schedule can also specify how the stimulation is delivered.

Figure 19:
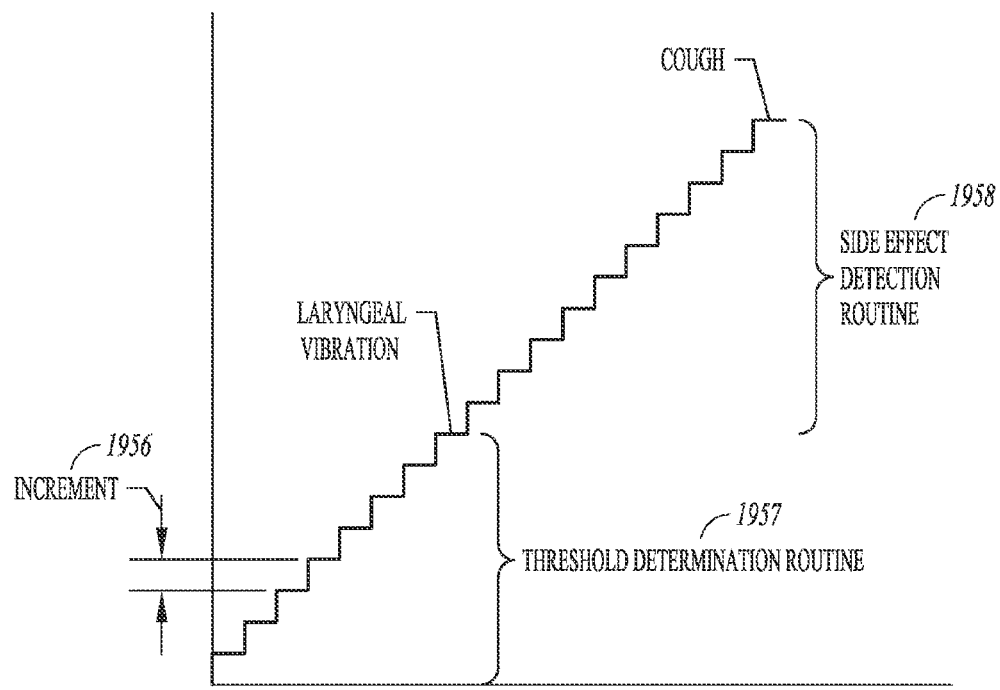
FIG. 19 illustrates an embodiment of a routine for finding threshold values for each of the electrode configurations.

FIG. 19 illustrates an embodiment of a routine for finding threshold values for each of the electrode configurations. The illustrated routine increases the intensity of the neural stimulation therapy over a period of time. The intensity is increased in increments 1956, which are not necessarily equal increments. In the illustrated embodiments, a threshold determination routine 1957 is performed to detect a lower boundary physiologic response to the neural stimulation such as a laryngeal vibration response. The laryngeal vibration may be desirable during a titration process as it confirms capture of the vagus nerve, and this value can be used to determine an appropriate stimulation for the neural stimulation above the lower boundary. In various embodiments, a side effect detection routine 1958 is performed to detect an upper boundary physiologic response (e.g. cough) to the neural stimulation. Thus, for example, some embodiments may set a neural stimulation intensity between the lower boundary (e.g. laryngeal vibration) and the upper boundary (e.g. cough), and may set a depletion block stimulation intensity at or slightly above the lower boundary (e.g. laryngeal vibration) but below the intensity of the neural stimulation intensity. Such a threshold routine avoids side effects above the upper boundary (e.g. cough) and also avoids side effects below the lower boundary (e.g. laryngeal vibration) that would otherwise occur without the depletion block. Some embodiments decrease the intensity of the NCT therapy over a period of time to detect the desired or undesired physiologic responses to the neural stimulation.

Some embodiments use sensors to detect the lower boundary (e.g. laryngeal vibration) and the upper boundary (e.g. cough or phrenic nerve capture). At least some of the sensors may be part of an implantable device, such as an implantable nerve stimulator used to stimulate the target nerve. In some embodiments, at least some of the sensors are part of a programmer/PSA (pacing system analyzer). Examples of sensors include a pressure sensor, an accelerometer, a minute ventilation sensor, an impedance sensor, a sensor configured to detect an electrocardiogram (EKG), a sensor configured to detect an electromyogram (EMG), and a blood pressure sensor. Some embodiments use feedback from a patient or physician. For example, a clicker pad with a pain assessment or other scale can be used to allow the patient to provide feedback as to whether the stimulation provides laryngeal vibration or other desired response and whether the stimulation provides cough or phrenic nerve capture or other undesired physiological response to the stimulation. The algorithm can be implemented in the programmer, or in the implantable device, or in an external device configured to communicate with the programmer and/or the implantable device such as in a patient management system.

Some system embodiments may be designed to sense laryngeal vibration to confirm capture of the vagus nerve, and then deliver a depletion block to the vagus nerve at an intensity (e.g. amplitude) selected to capture axons with lower stimulation thresholds to block the laryngeal vibration and also deliver a neural stimulation at an intensity (e.g. amplitude) selected to be higher than the depletion block stimulation to capture axons with a higher stimulation threshold and provide the desired physiological response for the delivered therapy. The confirmation of capture may be performed during an implantation procedure. Some implantable systems, such as systems implanted in an ambulatory patient to provide a chronic therapy for heart failure, hypertension, or other chronic condition, may be configured to interrupt a depletion block to confirm that the implantable system is capturing the vagus nerve. The confirmation process may be initiated in response to a command from a clinician or patient or according to a schedule.

Figure 20:
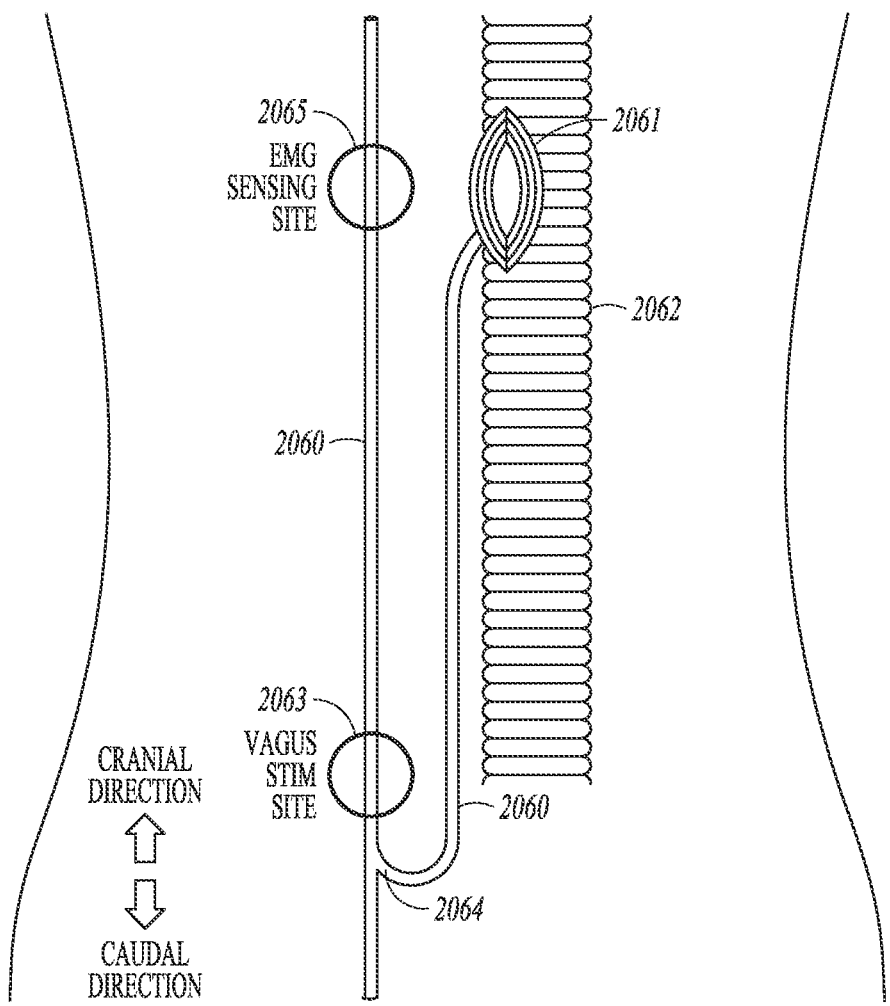
FIG. 20 illustrates an embodiment for verifying capture of a vagus nerve by sensing electromyogram (EMG) activity in laryngeal muscles.

The confirmation of capture may be accomplished a number of ways, including using external sensors, patient input, or clinician's observations. For example, a clinician may place fingers over the larynx to feel for laryngeal vibration. One example of a system that may be used to confirm capture is illustrated in FIG. 20, which generally illustrates a right vagus nerve 2059 and a recurrent laryngeal nerve 2060 branching off of the right vagus nerve to innervate the laryngeal muscles 2061 near the trachea 2062. There is also a left vagus nerve (not illustrated) and a recurrent laryngeal nerve (not illustrated) branching off of the left vagus nerve to innervate the laryngeal muscles near the trachea. The ability to verify capture of a vagus nerve through EMG sensing of activity in laryngeal muscles may be used with right and/or left vagus nerve stimulation. The recurrent laryngeal nerve branches off the vagus nerve at a position caudal to the laryngeal muscles, and then loops back cranially to innervate the laryngeal muscles. This loop is a relatively lengthy neural pathway that provides latency between the time of a vagus nerve stimulation pulse and the time of the activation of the laryngeal muscles. Because of this latency, the laryngeal activation can be measured by EMG sensors after the pulse without being blunted by the stimulation artifact. Further, the loop provides options for adjusting the distance between the vagus nerve stimulation site and the laryngeal muscles. For example, in the embodiment illustrated in FIG. 20, the stimulation electrodes may be placed to stimulate the vagus nerve at stimulation site 2063 relatively near the point 2064 where the recurrent laryngeal nerve branches off the vagus nerve, and the EMG sensor(s) can be positioned along the vagus nerve at EMG sensing site 2065 proximate to the laryngeal muscles to improve detection of activity in the laryngeal muscles and reduce the potential of interference from stimulation pulses. The stimulation electrodes and EMG sensor(s) may be on the same lead. Assuming a 0.17 ms/cm conduction rate for a 10 µm A-fiber that innervates the muscles of the larynx and assuming 50-60 cm of travel distance from the stimulated location of the vagus nerve into the recurrent laryngeal nerve and back up to the laryngeal muscles, the muscles of the larynx will activate about 8.33-10 ms after the vagus nerve is stimulated. Thus, the response of the laryngeal muscles to vagal nerve stimulation has a relatively long latency because of the relatively long travel distance. The actual distance from the stimulation site to the laryngeal muscles will depend on the location of the stimulation site and the specific anatomy of the patient. For example, taller people with longer necks may have longer recurrent laryngeal nerves. Patient specific templates may be developed to account for the specific anatomical differences in the patient.

Figure 21:
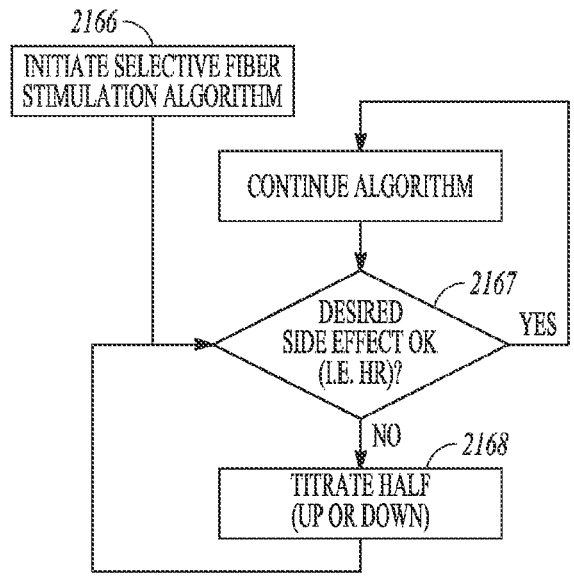
FIGS. 21-30 illustrate, by way of example and not limitation, some selective fiber stimulation processes that may be performed using the depletion block stimulation.

FIGS. 21-30 illustrate, by way of example and not limitation, some selective fiber stimulation processes that may be performed using the depletion block stimulation. FIG. 21 illustrates an example of a process to titrate the nerve stimulation (e.g. HALF stimulation) to obtain a desired response to the stimulation. The selective fiber stimulation algorithm may be initiated at 2166. A physiological parameter, such as heart rate, may be monitored at 2167 and the selective fiber stimulation algorithm continues to be implemented as long as the monitored parameter is acceptable. The nerve stimulation (e.g. HALF stimulation) is appropriately titrated when the monitored parameter is not acceptable so that the adjusted nerve stimulation again causes the monitored parameter to be acceptable.

Figure 22:
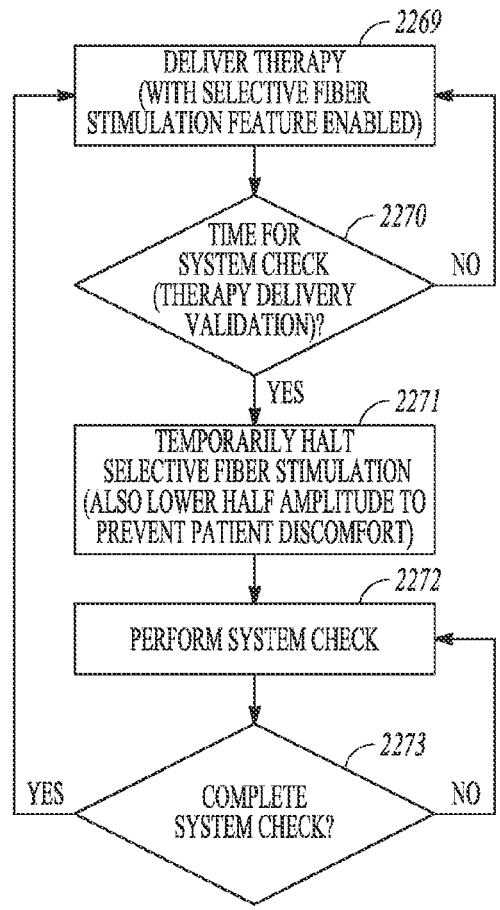

FIG. 22 illustrates an example of a process to validate therapy delivery. At 2269 the selective fiber stimulation is delivered as part of a therapy. As generally illustrated at 2270 the system checks to see if it is time to validate the therapy delivery. The validation process may be initiated by a clinician, may be initiated by a patient, or may be automatically-initiated by the system. Some embodiments that automatically initiated the validation process may be configured to allow the patient to disable the validation process. If it is time to validate, the depletion block may be temporarily halted at 2271. The neural stimulation may also be reduced to reduce patient discomfort that may otherwise result when the depletion block is halted. The patient may be monitored to validate that the neural stimulation is still capturing the nerve (e.g. "system check") at 2272. For example, some embodiments may check for laryngeal vibration to confirm vagal nerve stimulation. After the validation process is complete at 2273, the process may return to deliver the selective fiber stimulation. Some embodiments automatically enable the therapy.

Figure 23:
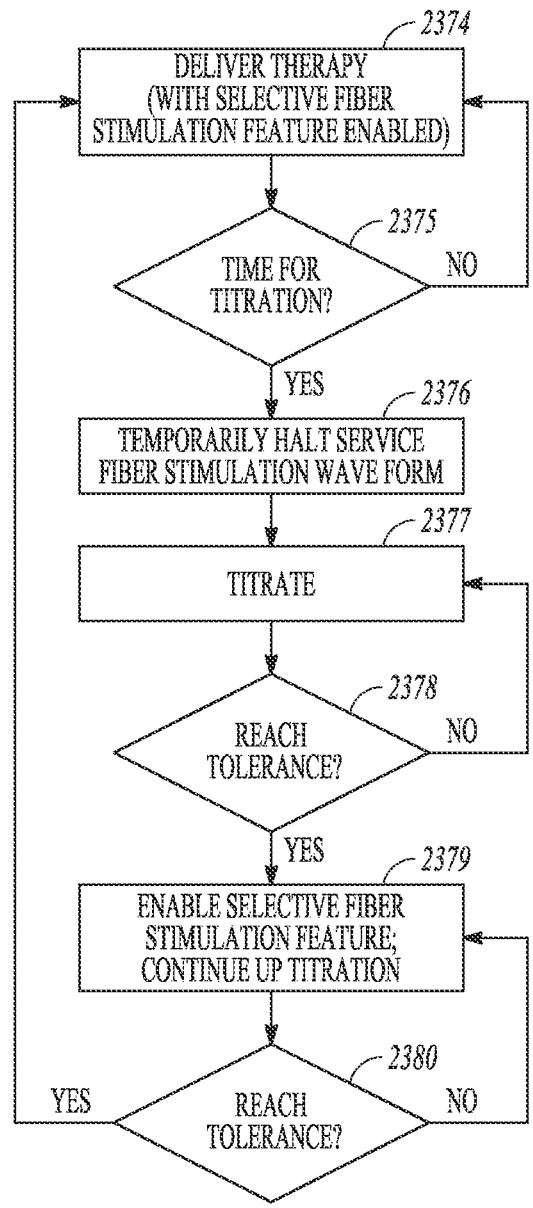

FIG. 23 illustrates an example of a process for up-titration a neural stimulation therapy. Different patients may have different tolerance levels for neural stimulation. Additionally, a patient may not be able to tolerate a therapy if the intensity of the therapy begins at the desired intensity level, but may be able to accommodate to the neural stimulation and be able to tolerate the therapy better if the intensity is increased over an extended period of time on the order of days or weeks or months. At 2374 the selective fiber stimulation may be delivered as part of a therapy. As generally illustrated at 2375 the system checks to see if it is time to titrate the therapy. The titration process may be initiated by a clinician, may be initiated by a patient, or may be automatically-initiated by the system. The titration process may be performed, where the depletion block stimulation may be halted at 2376 and the stimulation intensity is incremented and then delivered until the patient tolerates the increased stimulation without the depletion block. This process may continue until the patient is no longer able to tolerate the stimulation without the depletion block, at which time the intensity of the stimulation may be decremented back to a level which the patient could tolerate without the depletion block. The depletion block may be initiated and the up-titration process may continue at 2377, where the intensity of the stimulation is incremented and then delivered until the patient tolerates the increased stimulation with the depletion block. This process may continue until the patient is no longer able to tolerate the stimulation with the depletion block, at which time the intensity of the stimulation may be decremented back to a level which the patient could tolerate with the depletion block. A system may be configured to use these tolerance levels (with or without depletion block stimulation) to set the neural stimulation intensity and to limit the neural stimulation intensity if the intensity is adjustable during the therapy.

Figure 24:
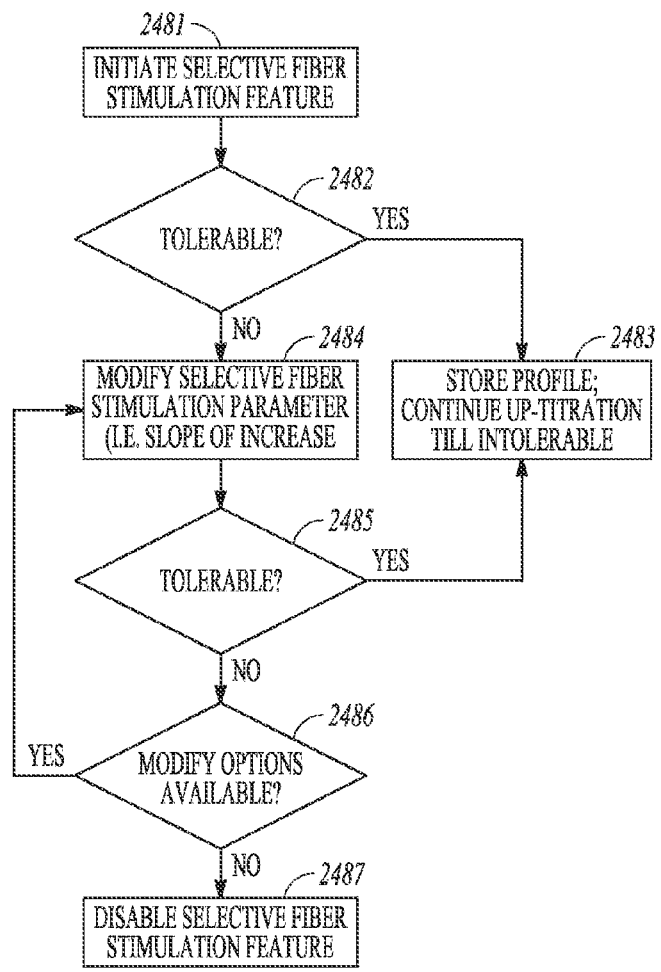

FIG. 24 illustrates an example of a process for adjusting depletion block stimulation. At 2481 the selective fiber stimulation may be delivered as part of a therapy, and then the process determines if the selective fiber stimulation is tolerable at 2482. If the stimulation is tolerable the depletion block stimulation parameters may be stored as illustrated at 2483 and the up-titration process to increment the intensity of the nerve stimulation may continue until the nerve stimulation is not tolerable. If the stimulation is not tolerable at 2482, the process may modify the depletion block parameters (e.g. frequency, pulse width and/or amplitude) at 2484 and determine if the stimulation is tolerable with the modified depletion stimulation parameters 2485. If the stimulation is not tolerable 2485 and if there are options available for modifying the depletion block stimulation 2486, then the process may return to 2484 to modify the depletion block parameters. The process may continue until there are no options available for further modification of the depletion block stimulation 2486 at which time the depletion block feature may be disabled 2487, or until the nerve stimulation with the depletion block stimulation is tolerable 2483. At 22483 the depletion block stimulation parameters may be stored and the up-titration process to increment the intensity of the nerve stimulation may continue until the nerve stimulation is not tolerable.

Figure 25:
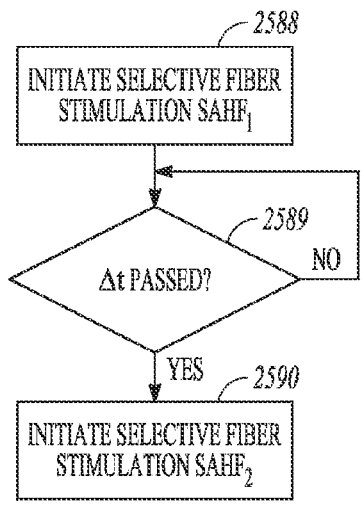

FIG. 25 illustrates an example of a process for implementing depletion block stimulation. At 2588 depletion block stimulation may be implemented using a first set of stimulation parameters. After a period of time has elapsed 2589, the depletion block stimulation may be implemented using a second set of stimulation parameters 2590. By way of example but not limitation, the first set of parameters for the depletion block stimulation may include a relatively high frequency (e.g. 400 Hz) to provide a quick block, and the second set of parameters for the depletion stimulation may include a relatively low frequency (e.g. 200 Hz) to reduce energy expenditure during the maintenance of the depletion block stimulation.

Figure 26:
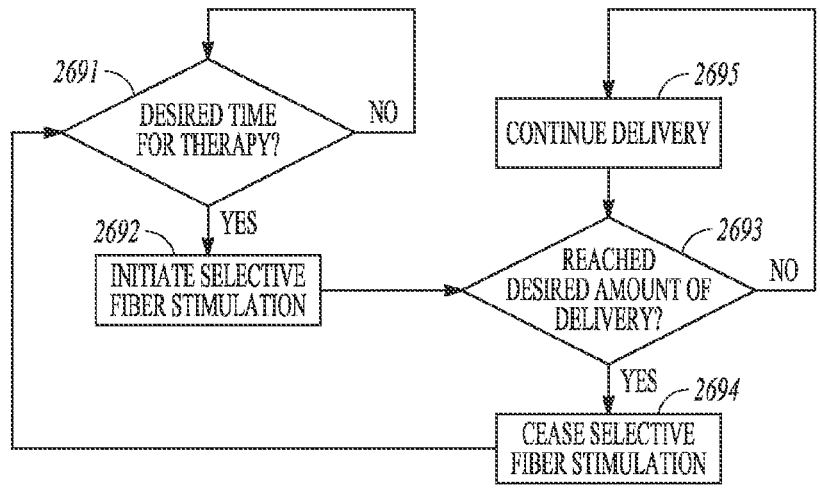

FIG. 26 illustrates an example of a process for delivering a dose of neural stimulation. At 2691 the system determines if there is a desired time for a dose of neural stimulation therapy. The dose for the neural stimulation therapy may be initiated by a clinician, may be initiated by a patient, or may be automatically-initiated by the system. When it is time for the dose of neural stimulation therapy the system initiates the selective neural stimulation at 2692, including both the nerve stimulation and the depletion block stimulation. At 2693 it may be determined if the desired amount of stimulation for the dose has been delivered. If the dose has been completed, the neural stimulation may stop at 2694, and the process may return to 2691 to await the next dose time. If the dose has not been completed, the neural stimulation may continue at 2695.

Figure 27:
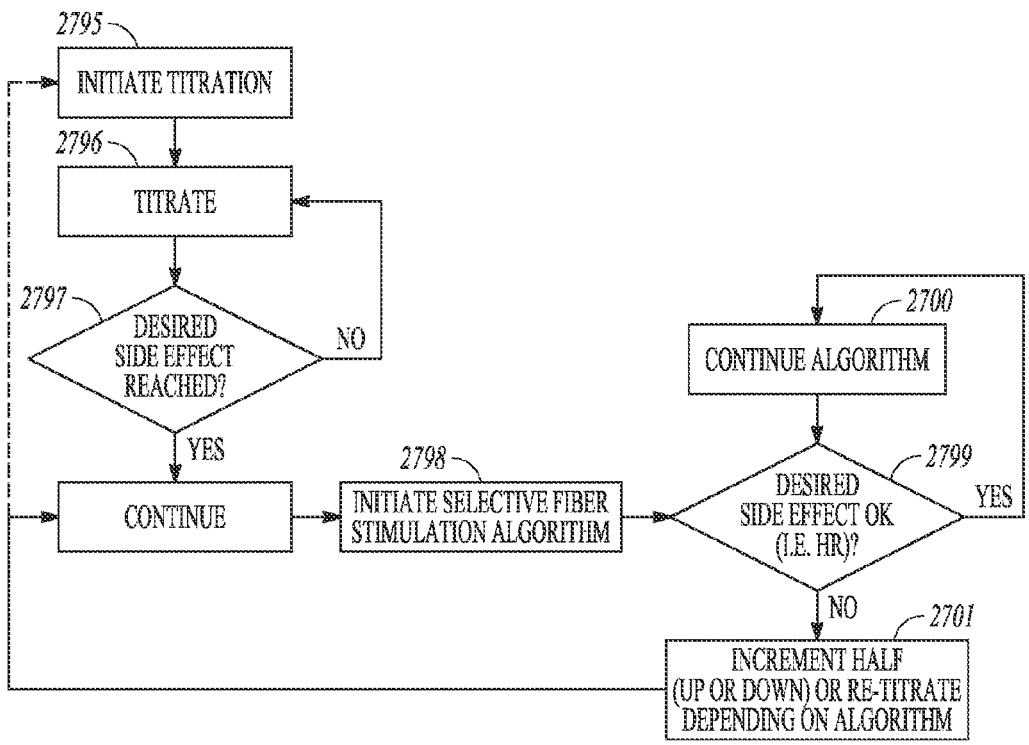

FIG. 27 illustrates an example of a process for setting the nerve stimulation and depletion block stimulation. At 2795 the nerve stimulation may be delivered and an up-titration process (2796 and 2797) maybe implemented until a desired physiologic response is reached. The process may continue by delivering depletion block stimulation 2798. An example of a desired physiologic response is a desired heart rate or blood pressure response to vagal stimulation. If the depletion block stimulation does not undesirably affect the desired physiologic response at 2799, the nerve stimulation may continue at 2700. If the depletion block stimulation undesirably affects the desired physiologic response at 2799, then at 2701 the nerve stimulation may adjusted at 2795 and 2796 or the depletion block may be adjusted and the adjusted depletion block may be delivered at 2798.

Figure 28:
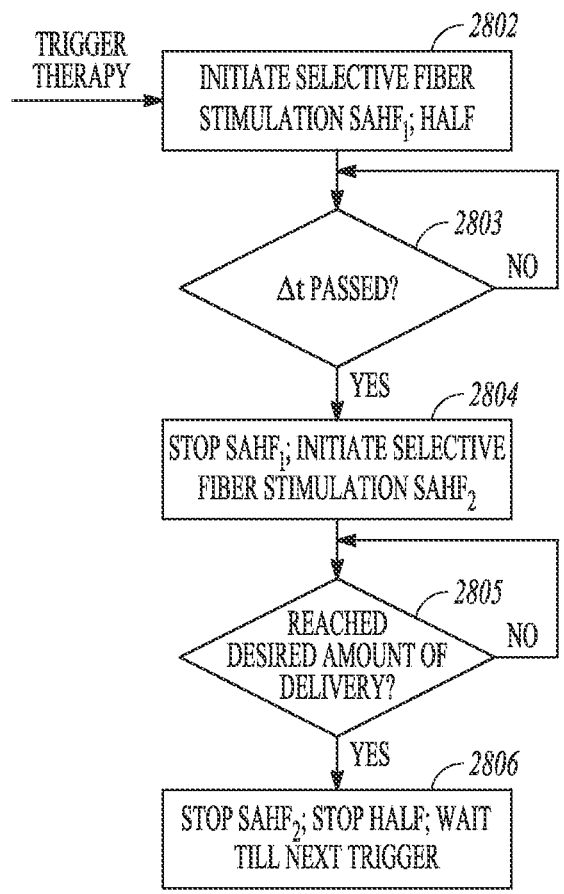

FIG. 28 illustrates an example of a process for delivering a dose of neural stimulation using more than one set of depletion block stimulation parameters. The depletion block (e.g. SAHF) and the nerve stimulation (e.g. HALF) may be initiated at 2802. The depletion block stimulation may be implemented using a first set of stimulation parameters. After a period of time has elapsed 2803, the depletion block stimulation may stop using the first set of stimulation parameters and may be implemented using a second set of stimulation parameters 2804. By way of example but not limitation, the first set of parameters for the depletion block stimulation may include a relatively high frequency (e.g. 400 Hz) to provide a quick block, and the second set of parameters for the depletion stimulation may include a relatively low frequency (e.g. 200 Hz) to reduce energy expenditure during the maintenance of the depletion block stimulation. At 2805 it may be determined if the desired amount of stimulation for the dose has been delivered. The stimulation continues until the dose is complete. If the dose has been completed, both the nerve stimulation and the depletion block stimulation may be stopped at 2806, and the process may return to 2802 to await a trigger for the next dose of therapy.

Figure 29:
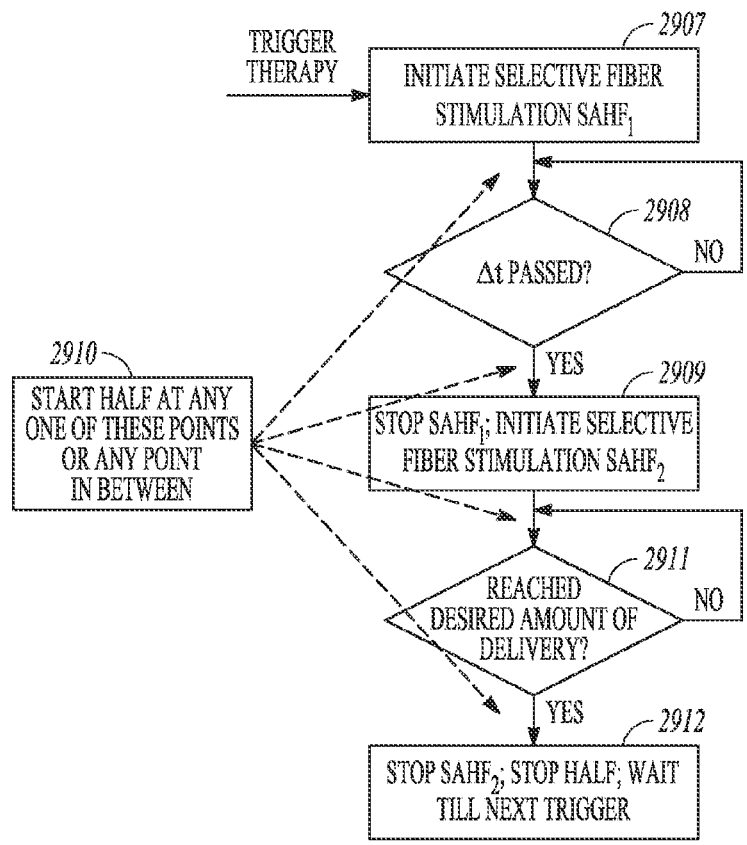

FIG. 29 illustrates an example of a process for implementing selective neural stimulation. At 2907 depletion block stimulation may be implemented using a first set of stimulation parameters (e.g. $SAHF_1$). After a period of time has elapsed 2908, the depletion block stimulation may stop using the first set of stimulation parameters and may be implemented using a second set of stimulation parameters (e.g. $SAHF_2$) 2909. By way of example but not limitation, the first set of parameters for the depletion block stimulation may include a relatively high frequency (e.g. 400 Hz) to provide a quick block, and the second set of parameters for the depletion stimulation may include a relatively low frequency (e.g. 200 Hz) to reduce energy expenditure during the maintenance of the depletion block stimulation. The nerve stimulation (e.g. HALF) 2910 may begin when the depletion block is initiated with the first set of parameters, may begin after the depletion block is initiated with the first set of parameters but before being implemented using the second set of parameters, or may begin after the depletion block is implemented using the second set of parameters. At 2911 it may be determined if the desired amount of stimulation for the dose has been delivered. The stimulation may continue until the dose is complete. If the dose has been completed, both the nerve stimulation and the depletion block stimulation may be stopped at 2912, and the process may return to 2907 to await a trigger for the next dose of therapy.

Figure 30:
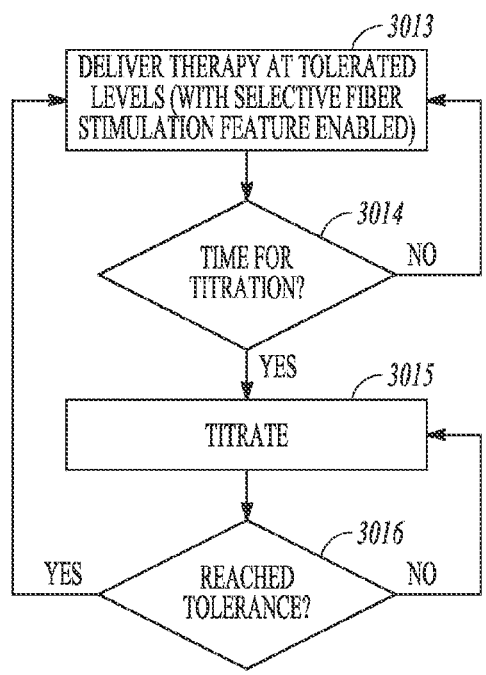

FIG. 30 illustrates an example of a process for titrating selective nerve stimulation. At 3013, a neural stimulation therapy with depletion block stimulation may be delivered at tolerated levels. A titration process may be initiated by a clinician, may be initiated by a patient, or may be automatically-initiated by the system. If it is time for titration at 3014 then a titration process such as an up-titration process may be implemented to determine a new tolerance threshold for the stimulation 3015. The process may return to 3013 to continue delivering selective nerve stimulation at settings corresponding to the new tolerance threshold for the stimulation. A goal of the titration process for the depletion block may include delivering the depletion block at currents as low as possible (to save battery) while retaining as much depletion block as necessary. A goal of the titration process for the nerve stimulation may include providing as much stimulation as possible to capture as many desired axons as possible, and avoiding excessive energy expenditure if the extra energy does not result in a significant number of additional desired axons being captured.

The present subject matter has been described with reference to vagus nerve stimulation for heart failure. However the present subject matter is not so limited. The present subject matter may be implemented for other therapies that involve stimulation of the vagus nerve or stimulation of other neural targets. Examples of such therapies include, but are not limited to, vagal nerve stimulation for inflammation disorders such as Crohn's disease, rheumatoid arthritis, multiple organ failure (i.e. Spanish flu; major burn), vagal nerve stimulation for epilepsy, depression, eating disorders and pain, spinal cord stimulation for pain and heart failure, baroreceptor stimulation, nerve stimulation for hypertension, peripheral nerve stimulation, occipital nerve stimulation for migraines, spasticity, asthma or chronic obstructive pulmonary disease.

FIGS. 31-34 illustrate system embodiments adapted to provide vagal stimulation, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. Further, systems may be designed to stimulate nerve targets other than the cervical vagus nerve. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve.

Figure 31:
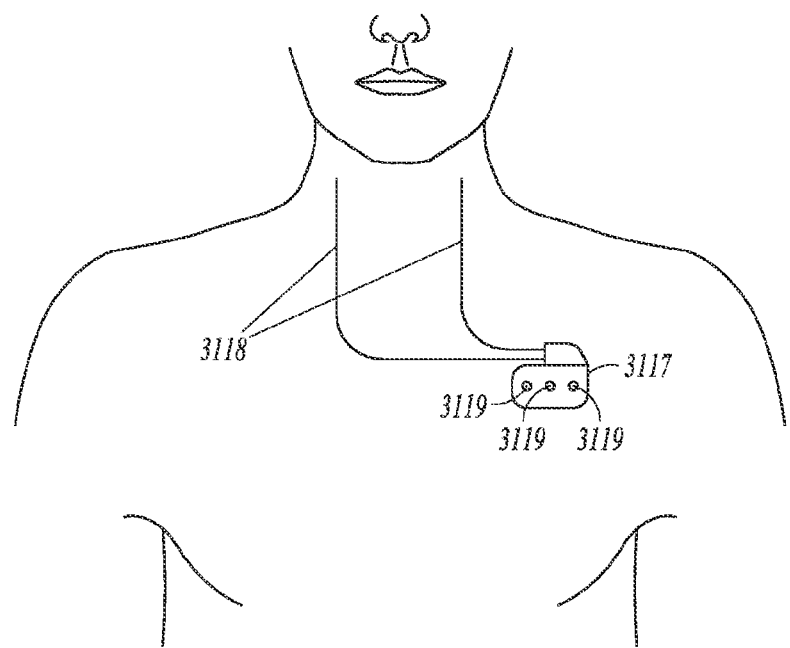
FIGS. 31-34 illustrate system embodiments adapted to provide vagal stimulation.

FIG. 31 illustrates a system embodiment in which an IMD 3117 is placed subcutaneously or submuscularly in a patient's chest with lead(s) 3118 positioned to stimulate a vagus nerve. According to various embodiments, neural stimulation lead(s) 3118 may be subcutaneously tunneled to a neural target. Some embodiments may have a nerve cuff electrode or helical electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. Other neural targets can be stimulated, such as cardiac nerves and cardiac fat pads. The illustrated system may include leadless ECG electrodes 3119 on the housing of the device. These ECG electrodes are capable of being used to detect heart rate and detecting portions of the cardiac cycle, for example.

Figure 32:
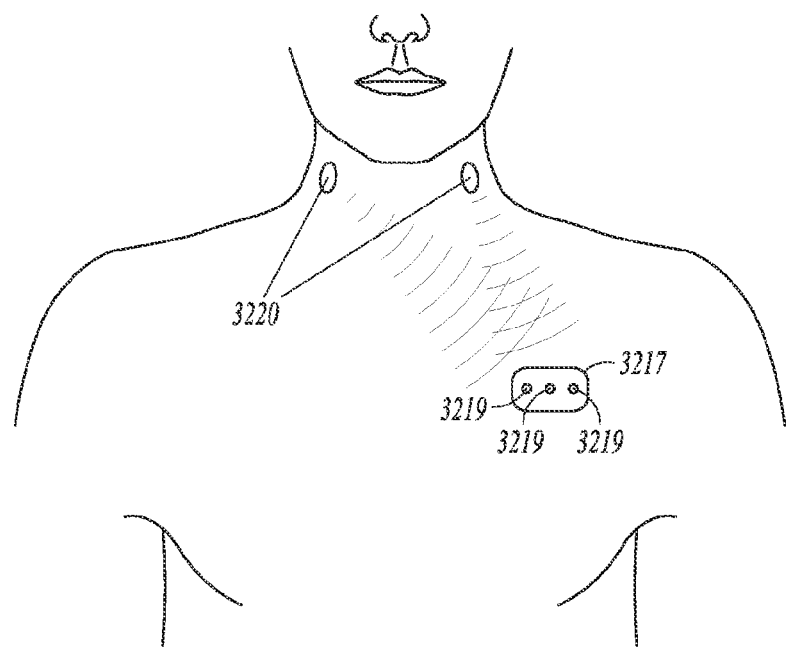

FIG. 32 illustrates a system embodiment that includes an implantable medical device (IMD) 3217 with satellite electrode(s) 3220 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. The system may include leadless ECG electrodes on the housing of the device. These ECG electrodes 3219 are capable of being used to detect heart rate and portions of the cardiac cycle, for example.

Figure 33:
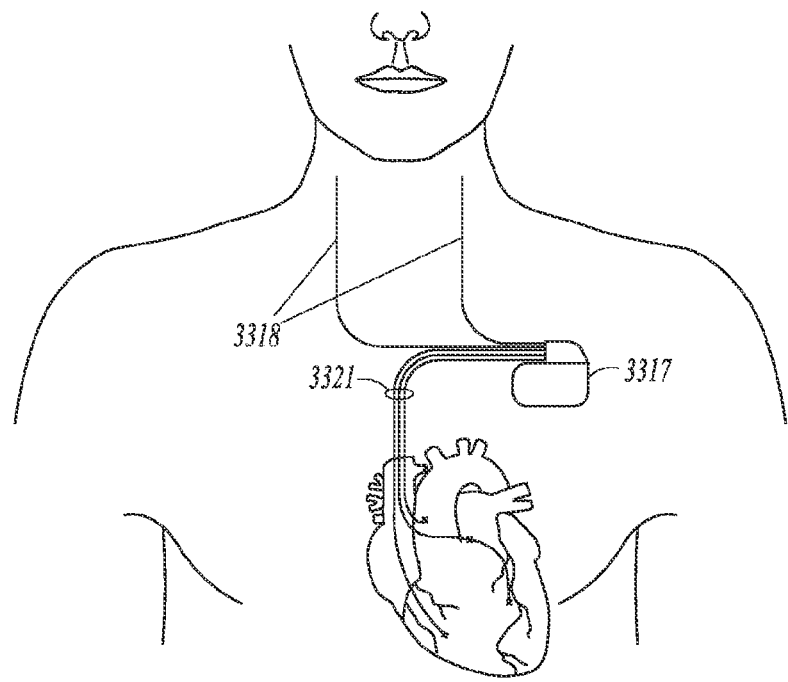

FIG. 33 illustrates an IMD 3317 placed subcutaneously or submuscularly in a patient's chest with lead(s) 3321 positioned to provide a CRM therapy to a heart, and with lead(s) 3318 positioned to stimulate and/or inhibit neural traffic at a neural target, such as a vagus nerve, according to various embodiments. According to various embodiments, neural stimulation lead(s) may be subcutaneously tunneled to a neural target. Some embodiments may have a nerve cuff electrode or helical electrode to stimulate the neural target. Some lead embodiments may be intravascularly fed into a vessel proximate to the neural target, and use transducer(s) within the vessel to transvascularly stimulate the neural target. For example, some embodiments may target the vagus nerve using electrode(s) positioned within the internal jugular vein.

Figure 34:
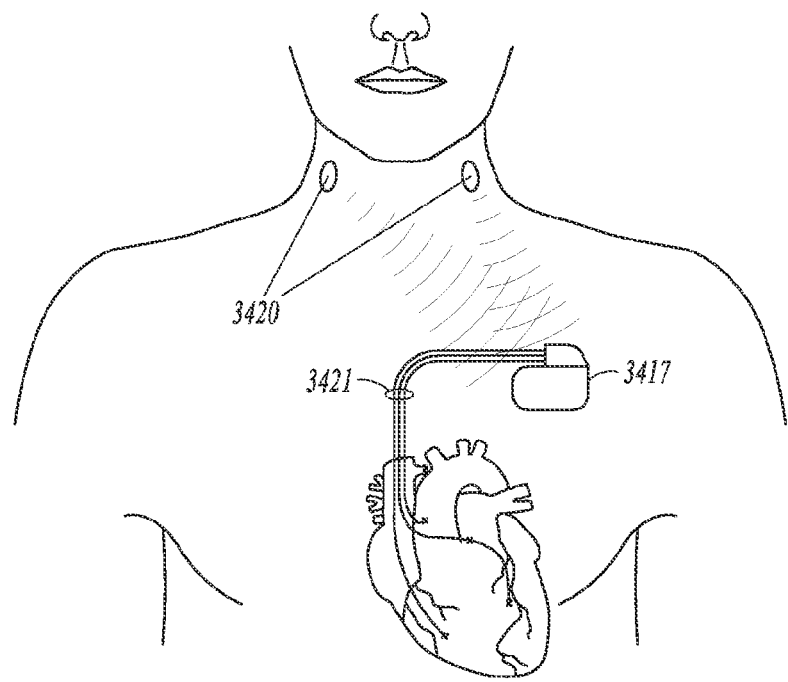

FIG. 34 illustrates an IMD 3417 with lead(s) 3421 positioned to provide a CRM therapy to a heart, and with satellite transducers 3420 positioned to stimulate/inhibit a neural target such as a vagus nerve, according to various embodiments. The satellite transducers may be operably in communication with the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links. Examples of satellite transducers include subcutaneous electrodes, nerve cuff electrodes and intravascular electrodes.

The above detailed description is intended to be illustrative, and not restrictive. The scope of the disclosure should, therefore, be determined with references to the appended claims, along with the full scope of equivalents to which such claims are entitled.

What is claimed is:

1. A system for selectively stimulating targeted axons in a neural target using at least one electrode operably adjacent to the neural target, where the neural target has a plurality of axons including the targeted axons that have activation thresholds for nerve activation at or below a first level and non-targeted axons that have activation thresholds for nerve activation at or below a second level, the second level being below the first level, the system comprising:

a stimulator configured to deliver electrical energy to the neural target using the at least one electrode, wherein the electrical energy delivered to the neural target includes both nerve stimulation having nerve stimulation parameters and depletion block stimulation having depletion block stimulation parameters,
the nerve stimulation parameters including an amplitude and a pulse width to depolarize all of a first set of axons in the plurality of axons and further including a nerve stimulation frequency, wherein the first set of axons include both the targeted axons and the non-targeted axons in the neural target, and
the depletion block stimulation parameters including a depletion pulse frequency extending from 100 Hz to 700 Hz and further including an amplitude and a pulse width to depolarize all of the second set of axons in the plurality of axons, the second set of axons being a subset of the first set of axons, the depletion pulse frequency being higher than the nerve stimulation frequency, wherein the second set of axons include non-targeted axons and do not include targeted axons,
wherein the stimulator and the at least one electrode are configured to induce action potentials at the nerve stimulation frequency in the first set of axons using the nerve stimulation having the nerve stimulation parameters, and are configured to induce action potentials at the depletion pulse frequency only in the second set of axons using the depletion block stimulation having the depletion block stimulation parameters to deplete neurotransmitters and prevent the action potentials in the second set of axons from being communicated across a synaptic cleft; and
at least one controller configured to communicate with the stimulator and control the depletion block stimulation and the nerve stimulation such that a depletion nerve block is delivered to the non-targeted axons of the neural target while delivering nerve stimulation to the targeted axons.

2. The system of claim 1, wherein the at least one electrode includes a first electrode and a second electrode, and the stimulator is configured to deliver the neural stimulation to the neural target using the first electrode and the second electrode, and to deliver depletion block stimulation to the neural target using the first electrode and the second electrode.

3. The system of claim 1, wherein the at least one electrode includes a first electrode, a second electrode, a third electrode and a fourth electrode, and the stimulator is configured to deliver the neural stimulation to the neural target using the first electrode and the second electrode, and to deliver depletion block stimulation to the neural target using the third electrode and the fourth electrode.

4. The system of claim 1, the at least one electrode includes a first electrode, a second electrode, and a third electrode, and wherein the stimulator is configured to deliver neural stimulation to the neural target using the first electrode and the second electrode, and to deliver depletion block stimulation to the neural target using the second electrode and the third electrode.

5. The system of claim 1, wherein the amplitude within the nerve stimulation parameters is higher than the amplitude within the depletion block stimulation parameters.

6. The system of claim 1, wherein the controller is configured to:

control the depletion block stimulation and the nerve stimulation to provide intermittent neural stimulation with alternating stimulation ON periods and stimulation OFF periods;

deliver the nerve stimulation to capture the first set of axons during stimulation ON periods and not during stimulation OFF periods; and deliver depletion block stimulation to capture the second set of axons during the stimulation ON periods and not during the stimulation OFF periods.

7. The system of claim 6, further comprising a physiologic sensor configured to sense a physiologic parameter, the controller operably connected to the sensor to detect a physiologic event from the sensed physiologic parameter, the controller further configured to trigger timing for the intermittent stimulation based on the detected physiologic event.

8. The system of claim 6, wherein the neural target includes a cervical region of a vagus nerve, the second set of axons includes A-type motor fibers.

9. The system of claim 8, wherein at least some of the axons in the first set of axons are B-type fibers, and the second set excludes at least some the B-type fibers in the first set.

10. The system of claim 1, wherein the controller is configured to initiate delivery of the depletion block stimulation before initiating delivery of the nerve stimulation.

11. The system of claim 10, wherein the stimulation ON periods are for a time period within a range between a ¼ of a second and 150 seconds, and the stimulation OFF periods are for a time period between 1 second and 150 seconds.

12. The system of claim 1, wherein the controller is configured to implement a programmed titration routine, and to implement the programmed titration routine, the controller is configured to interrupt delivery of the stimulation to the nerve, adjust at least one of the nerve stimulation or the depletion block stimulation during the interruption, and reinstate delivery of the stimulation to the nerve.

13. The system of claim 12, wherein to adjust the at least one of the nerve stimulation or the depletion block stimulation, the controller is configured to adjust at least one of an amplitude of the nerve stimulation or an amplitude of the depletion block stimulation.

14. The system of claim 12, wherein to adjust the at least one of the nerve stimulation or the depletion block stimulation the controller is configured to adjust at least one of a pulse width for the series of pulses in the nerve stimulation or a pulse width for the series of pulses in the depletion stimulation.

15. A method for selectively stimulating targeted axons in a neural target by delivering electrical energy to the neural target using at least one electrode operably adjacent to the neural target, where the neural target has a plurality of axons including the targeted axons that have activation thresholds for nerve activation at or below a first level and non-targeted axons that have activation thresholds for nerve activation at or below a second level, the second level being below the first level, the method comprising:

inducing action potentials at a nerve stimulation frequency in the a first set of axons in the neural target by delivering nerve stimulation having nerve stimulation parameters, the nerve stimulation parameters including the nerve stimulation frequency, an amplitude and a pulse width to depolarize all of the first set of axons in the plurality of axons, wherein the first set of axons include both the targeted axons and the non-targeted axons in the neural target; and inducing action potentials at a depletion pulse frequency only in a second set of axons in the neural target by delivering depletion block stimulation having depletion block stimulation parameters, the depletion block stimulation parameters including the depletion pulse frequency extending from 100 Hz to 700 Hz and further having an amplitude and a pulse width to depolarize only the second set of axons in the plurality of axons, the second set of axons being a subset of the first set of axons, the depletion pulse frequency being higher than the nerve stimulation frequency, wherein the second set of axons include non-targeted axons and do not include targeted axons wherein delivering the depletion block stimulation depletes neurotransmitters and prevents the action potentials in the second set of axons from being communicated across a synaptic cleft, such that a depletion nerve block is delivered to the non-targeted axons while delivering nerve stimulation to the targeted axons.

16. The method of claim 15, further comprising determining the second level for the activation thresholds for the non-targeted axons, and using the determined second level and to set the depletion block stimulation parameters to depolarize all of the second set of axons in the plurality of axons.

17. The method of claim 15, wherein delivering nerve stimulation includes delivering stimulation at an amplitude higher than the depletion block stimulation.

18. The method of claim 15, wherein delivering stimulation to the nerve includes delivering intermittent neural stimulation with alternating stimulation ON periods and stimulation OFF periods, wherein:

delivering nerve stimulation configured to capture the first set of axons in the nerve includes delivering the series of electrical pulses at the stimulation pulse frequency during stimulation ON periods and not during stimulation OFF periods; and delivering the depletion block stimulation includes delivering the series of electrical pulses at the depletion pulse frequency during the stimulation ON periods and not during the stimulation OFF periods.

19. The method of claim 15, wherein delivering the depletion block and delivering the nerve stimulation includes initiating delivery of the presynaptic depletion block before initiating delivery of the nerve stimulation.

20. The method of claim 15, wherein delivering stimulation to the nerve includes delivering stimulation to a cervical region of a vagus nerve, the second set of axons includes A-type motor fibers.

* * * * *